United States Patent
Moffatt et al.

(10) Patent No.: US 9,175,299 B2
(45) Date of Patent: Nov. 3, 2015

(54) MUTATION INVOLVED IN INCREASED TOLERANCE TO IMIDAZOLINONE HERBICIDES IN PLANTS

(75) Inventors: John Moffatt, Cheney, WA (US); Rob Bruns, Fort Collins, CO (US); Iwona Birk, Raleigh, NC (US); Bijay Singh, Cary, NC (US)

(73) Assignee: BASF AGROCHEMICAL PRODUCTS, B.V., Arnhem (NL)

(*) Notice: Subject to any disclaimer, the term of this patent is extended or adjusted under 35 U.S.C. 154(b) by 1509 days.

(21) Appl. No.: 11/720,569

(22) PCT Filed: Dec. 1, 2005

(86) PCT No.: PCT/US2005/043577
§ 371 (c)(1),
(2), (4) Date: Aug. 11, 2008

(87) PCT Pub. No.: WO2006/060634
PCT Pub. Date: Jun. 8, 2006

(65) Prior Publication Data
US 2009/0029860 A1    Jan. 29, 2009

Related U.S. Application Data

(60) Provisional application No. 60/632,376, filed on Dec. 1, 2004.

(51) Int. Cl.
*A01H 5/10* (2006.01)
*C12N 15/82* (2006.01)
*C12N 9/10* (2006.01)

(52) U.S. Cl.
CPC ............ *C12N 15/821* (2013.01); *C12N 9/1022* (2013.01); *C12N 15/8274* (2013.01)

(58) Field of Classification Search
None
See application file for complete search history.

(56) References Cited

U.S. PATENT DOCUMENTS

| | | | |
|---|---|---|---|
| 5,013,659 A * | 5/1991 | Bedbrook et al. | 536/23.2 |
| 6,013,659 A | 1/2000 | Goldfarb et al. | |
| 2003/0097692 A1 | 5/2003 | Jander et al. | |
| 2007/0033670 A1 * | 2/2007 | Konzak et al. | 800/278 |

FOREIGN PATENT DOCUMENTS

| | | | |
|---|---|---|---|
| WO | 0192512 A2 | | 6/2001 |
| WO | WO 02/08794 | * | 1/2002 |
| WO | WO 03/014356 | * | 2/2003 |
| WO | WO 03/014356 A1 | | 2/2003 |
| WO | WO 03/014357 | | 2/2003 |
| WO | WO 2004/001673 A2 | * | 2/2004 |
| WO | WO 2004/016073 | | 2/2004 |

OTHER PUBLICATIONS

Zhu et al 2000, Nature Biotechnology 18: 555-558.*
Genbank Accession No. AY210407 Mar. 10, 2003, Pozniak et al.*
Barclay et al, Molecular Biology 2008, 22: 217-225.*
Li D. et al., "A mutation at the Ala122 position of acetohydroxyacid synthase (AHAS) located on chromosome 6D of wheat: improved resistance to imidazolinone and a faster assay for marker assisted selection," Mol. Breeding, 22:217-225 (2008).

* cited by examiner

*Primary Examiner* — David H Kruse
(74) *Attorney, Agent, or Firm* — Mintz, Levin, Cohn, Ferris, Glovsky And Popeo, P.C.

(57) ABSTRACT

The present invention is directed to nucleic acids encoding polypeptides that confer upon a plant tolerance to an imidazolinone and/or other acetohydroxyacid synthase (AHAS) inhibiting herbicide when expressed in the plant. The present invention also provides plants having increased tolerance to an imidazolinone and/or other AHAS-inhibiting herbicide. More particularly, the present invention includes plants containing at least one IMI nucleic acid. The present invention also includes seeds produced by these plants and methods of controlling weeds in the vicinity of these wheat plants.

17 Claims, 7 Drawing Sheets

FIG. 1

|               |       | 1                                                  50 |
|---------------|-------|--------------------------------------------------------|
| Shiloh8-Als1  | (1)   | TCCCCCGCCGCCACCTCCGCCGCGCCTCCCGCAACCGCGCTCCGGCCCTG     |
| Shiloh-Als1   | (1)   | TCCCCCGCCGCCACCTCCGCCGCGCCTCCCGCAACCGCGCTCCGGCCCTG     |
| Consensus     | (1)   | TCCCCCGCCGCCACCTCCGCCGCGCCTCCCGCAACCGCGCTCCGGCCCTG     |

|               |       | 51                                                 100 |
|---------------|-------|--------------------------------------------------------|
| Shiloh8-Als1  | (51)  | GGGCCCGTCCGAGCCCCGCAAGGGCGCCGACATCCTCGTCGAGGCGCTCG     |
| Shiloh-Als1   | (51)  | GGGCCCGTCCGAGCCCCGCAAGGGCGCCGACATCCTCGTCGAGGCGCTCG     |
| Consensus     | (51)  | GGGCCCGTCCGAGCCCCGCAAGGGCGCCGACATCCTCGTCGAGGCGCTCG     |

|               |       | 101                                                150 |
|---------------|-------|--------------------------------------------------------|
| Shiloh8-Als1  | (101) | AGCGCTGCGGCATCGTCGACGTCTTCGCCTACCCCGGCGGCACCTCCATG |
| Shiloh-Als1   | (101) | AGCGCTGCGGCATCGTCGACGTCTTCGCCTACCCCGGCGGCGCCTCCATG |
| Consensus     | (101) | AGCGCTGCGGCATCGTCGACGTCTTCGCCTACCCCGGCGGC CCTCCATG     |

|               |       | 151                                                200 |
|---------------|-------|--------------------------------------------------------|
| Shiloh8-Als1  | (151) | GAGATCCACCAGGCGCTGACGCGCTCGCCCGTCATCACCAACCACCTCTT     |
| Shiloh-Als1   | (151) | GAGATCCACCAGGCGCTGACGCGCTCGCCCGTCATCACCAACCACCTCTT     |
| Consensus     | (151) | GAGATCCACCAGGCGCTGACGCGCTCGCCCGTCATCACCAACCACCTCTT     |

|               |       | 201                                                250 |
|---------------|-------|--------------------------------------------------------|
| Shiloh8-Als1  | (201) | CCGCCACGAGCAGGGGGAGGCGTTCGCGGCGTCCGGCTACGCCCGCGCGT     |
| Shiloh-Als1   | (201) | CCGCCACGAGCAGGGGGAGGCGTTCGCGGCGTCCGGCTACGCCCGCGCGT     |
| Consensus     | (201) | CCGCCACGAGCAGGGGGAGGCGTTCGCGGCGTCCGGCTACGCCCGCGCGT     |

|               |       | 251                                                300 |
|---------------|-------|--------------------------------------------------------|
| Shiloh8-Als1  | (251) | CCGGCCGCGTCGGCGTCTGCGTCGCCACCTCCGGCCCGGGGGCCACCAAC     |
| Shiloh-Als1   | (251) | CCGGCCGCGTCGGCGTCTGCGTCGCCACCTCCGGCCCGGGGGCCACCAAC     |
| Consensus     | (251) | CCGGCCGCGTCGGCGTCTGCGTCGCCACCTCCGGCCCGGGGGCCACCAAC     |

|               |       | 301                                                350 |
|---------------|-------|--------------------------------------------------------|
| Shiloh8-Als1  | (301) | CTCGTCTCCGCGCTCGCCGACGCCCTCCTCGACTCCATCCCCATGGTCGC     |
| Shiloh-Als1   | (301) | CTCGTCTCCGCGCTCGCCGACGCCCTCCTCGACTCCATCCCCATGGTCGC     |
| Consensus     | (301) | CTCGTCTCCGCGCTCGCCGACGCCCTCCTCGACTCCATCCCCATGGTCGC     |

|               |       | 351                                                400 |
|---------------|-------|--------------------------------------------------------|
| Shiloh8-Als1  | (351) | CATCACGGGCCAGGTCCCCCGCCGCATGATCGGCACGGACGCGTTCCAGG     |
| Shiloh-Als1   | (351) | CATCACGGGCCAGGTCCCCCGCCGCATGATCGGCACGGACGCGTTCCAGG     |
| Consensus     | (351) | CATCACGGGCCAGGTCCCCCGCCGCATGATCGGCACGGACGCGTTCCAGG     |

|               |       | 401                                                450 |
|---------------|-------|--------------------------------------------------------|
| Shiloh8-Als1  | (401) | AGACGCCCATAGTGGAGGTCACGCGCTCCATCACCAAGCACAACTACCTG     |
| Shiloh-Als1   | (401) | AGACGCCCATAGTGGAGGTCACGCGCTCCATCACCAAGCACAACTACCTG     |
| Consensus     | (401) | AGACGCCCATAGTGGAGGTCACGCGCTCCATCACCAAGCACAACTACCTG     |

|               |       | 451                                                500 |
|---------------|-------|--------------------------------------------------------|
| Shiloh8-Als1  | (451) | GTCCTTGACGTGGAGGATATCCCCCGCGTCATCCAGGAAGCCTTCTTCCT     |
| Shiloh-Als1   | (451) | GTCCTTGACGTGGAGGATATCCCCCGCGTCATCCAGGAAGCCTTCTTCCT     |
| Consensus     | (451) | GTCCTTGACGTGGAGGATATCCCCCGCGTCATCCAGGAAGCCTTCTTCCT     |

FIG. 1 continued

```
                      501                                                550
Shiloh8-Als1  (501) TGCATCCTCTGGCCGCCCGGGGCCGGTGCTAGTTGATATCCCCAAGGACA
Shiloh-Als1   (501) TGCATCCTCTGGCCGCCCGGGGCCGGTGCTAGTTGATATCCCCAAGGACA
Consensus     (501) TGCATCCTCTGGCCGCCCGGGGCCGGTGCTAGTTGATATCCCCAAGGACA 551                                                600
Shiloh8-Als1  (551) TCCAGCAGCAGATGGCTGTGCCCGTCTGGGACACTCCAATGAGTTTGCCA
Shiloh-Als1   (551) TCCAGCAGCAGATGGCTGTGCCCGTCTGGGACACTCCAATGAGTTTGCCA
Consensus     (551) TCCAGCAGCAGATGGCTGTGCCCGTCTGGGACACTCCAATGAGTTTGCCA 601                                                650
Shiloh8-Als1  (601) GGGTACATCGCCCGCCTGCCCAAGCCACCATCTACTGAATCGCTTGAGCA
Shiloh-Als1   (601) GGGTACATCGCCCGCCTGCCCAAGCCACCATCTACTGAATCGCTTGAGCA
Consensus     (601) GGGTACATCGCCCGCCTGCCCAAGCCACCATCTACTGAATCGCTTGAGCA 651                                                700
Shiloh8-Als1  (651) GGTCCTGCGTCTGGTTGGCGAGTCACGGCGCCCAATTCTGTATGTTGGTG
Shiloh-Als1   (651) GGTCCTGCGTCTGGTTGGCGAGTCACGGCGCCCAATTCTGTATGTTGGTG
Consensus     (651) GGTCCTGCGTCTGGTTGGCGAGTCACGGCGCCCAATTCTGTATGTTGGTG 701                                                750
Shiloh8-Als1  (701) GTGGCTGCGCTGCGTCTGGCGAGGAGTTGCGCCGCTTTGTTGAGCTTACT
Shiloh-Als1   (701) GTGGCTGCGCTGCGTCTGGCGAGGAGTTGCGCCGCTTTGTTGAGCTTACT
Consensus     (701) GTGGCTGCGCTGCGTCTGGCGAGGAGTTGCGCCGCTTTGTTGAGCTTACT 751                                                800
Shiloh8-Als1  (751) GGGATTCCAGTTACAACTACTCTGATGGGCCTTGGCAACTTCCCCAGCGA
Shiloh-Als1   (751) GGGATTCCAGTTACAACTACTCTGATGGGCCTTGGCAACTTCCCCAGCGA
Consensus     (751) GGGATTCCAGTTACAACTACTCTGATGGGCCTTGGCAACTTCCCCAGCGA 801                                                850
Shiloh8-Als1  (801) CGACCCACTGTCTCTGCGCATGCTTGGGATGCATGGCACTGTGTATGCAA
Shiloh-Als1   (801) CGACCCACTGTCTCTGCGCATGCTTGGGATGCATGGCACTGTGTATGCAA
Consensus     (801) CGACCCACTGTCTCTGCGCATGCTTGGGATGCATGGCACTGTGTATGCAA 851                                                900
Shiloh8-Als1  (851) ATTATGCAGTAGATAAGGCTGACCTGTTGCTCGCATTTGGTGTGCGGTTT
Shiloh-Als1   (851) ATTATGCAGTAGATAAGGCTGACCTGTTGCTCGCATTTGGTGTGCGGTTT
Consensus     (851) ATTATGCAGTAGATAAGGCTGACCTGTTGCTCGCATTTGGTGTGCGGTTT 901                                                950
Shiloh8-Als1  (901) GATGATCGTGTGACTGGGAAAATCGAGGCTTTTGCAAGCAGGTCCAAGAT
Shiloh-Als1   (901) GATGATCGTGTGACTGGGAAAATCGAGGCTTTTGCAAGCAGGTCCAAGAT
Consensus     (901) GATGATCGTGTGACTGGGAAAATCGAGGCTTTTGCAAGCAGGTCCAAGAT 951                                               1000
Shiloh8-Als1  (951) TGTGCACATTGACATTGACCCAGCTGAGATTGGCAAGAACAAGCAGCCAC
Shiloh-Als1   (951) TGTGCACATTGACATTGACCCAGCTGAGATTGGCAAGAACAAGCAGCCAC
Consensus     (951) TGTGCACATTGACATTGACCCAGCTGAGATTGGCAAGAACAAGCAGCCAC 1001                                               1050
Shiloh8-Als1 (1001) ATGTCTCCATTTGTGCAGATGTTAAGCTTGCTTTACAGGGGTTGAATGAT
Shiloh-Als1  (1001) ATGTCTCCATTTGTGCAGATGTTAAGCTTGCTTTACAGGGGTTGAATGAT
Consensus    (1001) ATGTCTCCATTTGTGCAGATGTTAAGCTTGCTTTACAGGGGTTGAATGAT
```

FIG. 1 continued

```
                          1051                                    1100
Shiloh8-Als1   (1051) CTATTAAATGGGAGCAAAGCACAACAGGGTCTGGATTTTGGTCCATGGCA
 Shiloh-Als1   (1051) CTATTAAATGGGAGCAAAGCACAACAGGGTCTGGATTTTGGTCCATGGCA
   Consensus   (1051) CTATTAAATGGGAGCAAAGCACAACAGGGTCTGGATTTTGGTCCATGGCA 1101                                    1150
Shiloh8-Als1   (1101) CAAGGAGTTGGATCAGCAGAAGAGGGAGTTTCCTCTAGGATTCAAGACTT
 Shiloh-Als1   (1101) CAAGGAGTTGGATCAGCAGAAGAGGGAGTTTCCTCTAGGATTCAAGACTT
   Consensus   (1101) CAAGGAGTTGGATCAGCAGAAGAGGGAGTTTCCTCTAGGATTCAAGACTT 1151                                    1200
Shiloh8-Als1   (1151) TTGGCGAGGCCATCCCGCCGCAATATGCTATCCAGGTACTGGATGAGCTG
 Shiloh-Als1   (1151) TTGGCGAGGCCATCCCGCCGCAATATGCTATCCAGGTACTGGATGAGCTG
   Consensus   (1151) TTGGCGAGGCCATCCCGCCGCAATATGCTATCCAGGTACTGGATGAGCTG 1201                                    1250
Shiloh8-Als1   (1201) ACAAAAGGGGAGGCGATCATTGCCACTGGTGTTGGGCAGCACCAGATGTG
 Shiloh-Als1   (1201) ACAAAAGGGGAGGCGATCATTGCCACTGGTGTTGGGCAGCACCAGATGTG
   Consensus   (1201) ACAAAAGGGGAGGCGATCATTGCCACTGGTGTTGGGCAGCACCAGATGTG 1251                                    1300
Shiloh8-Als1   (1251) GGCGGCTCAGTATTACACTTACAAGCGGCCACGGCAGTGGCTGTCTTCGT
 Shiloh-Als1   (1251) GGCGGCTCAGTATTACACTTACAAGCGGCCACGGCAGTGGCTGTCTTCGT
   Consensus   (1251) GGCGGCTCAGTATTACACTTACAAGCGGCCACGGCAGTGGCTGTCTTCGT 1301                                    1350
Shiloh8-Als1   (1301) CTGGTTTGGGGGCAATGGGATTTGGGTTACCAGCTGCAGCTGGCGCTGCT
 Shiloh-Als1   (1301) CTGGTTTGGGGGCAATGGGATTTGGGTTACCAGCTGCAGCTGGCGCTGCT
   Consensus   (1301) CTGGTTTGGGGGCAATGGGATTTGGGTTACCAGCTGCAGCTGGCGCTGCT 1351                                    1400
Shiloh8-Als1   (1351) GTGGCCAACCCAGGTGTTACAGTTGTTGACATTGATGGTGATGGTAGTTT
 Shiloh-Als1   (1351) GTGGCCAACCCAGGTGTTACAGTTGTTGACATTGATGGTGATGGTAGTTT
   Consensus   (1351) GTGGCCAACCCAGGTGTTACAGTTGTTGACATTGATGGTGATGGTAGTTT 1401                                    1450
Shiloh8-Als1   (1401) CCTCATGAACATTCAGGAGTTGGCGTTGATCCGCATTGAGAACCTCCCAG
 Shiloh-Als1   (1401) CCTCATGAACATTCAGGAGTTGGCGTTGATCCGCATTGAGAACCTCCCAG
   Consensus   (1401) CCTCATGAACATTCAGGAGTTGGCGTTGATCCGCATTGAGAACCTCCCAG 1451                                    1500
Shiloh8-Als1   (1451) TGAAGGTGATGATATTGAACAACCAGCATCTGGGAATGGTGGTGCAGTGG
 Shiloh-Als1   (1451) TGAAGGTGATGATATTGAACAACCAGCATCTGGGAATGGTGGTGCAGTGG
   Consensus   (1451) TGAAGGTGATGATATTGAACAACCAGCATCTGGGAATGGTGGTGCAGTGG 1501                                    1550
Shiloh8-Als1   (1501) GAGGATAGGTTTTACAAGGCCAATCGGGCGCACACATACCTTGGCAACCC
 Shiloh-Als1   (1501) GAGGATAGGTTTTACAAGGCCAATCGGGCGCACACATACCTTGGCAACCC
   Consensus   (1501) GAGGATAGGTTTTACAAGGCCAATCGGGCGCACACATACCTTGGCAACCC 1551                                    1600
Shiloh8-Als1   (1551) AGAAAATGAGAGTGAGATATATCCAGATTTTGTGACGATTGCTAAAGGAT
 Shiloh-Als1   (1551) AGAAAATGAGAGTGAGATATATCCAGATTTTGTGACGATTGCTAAAGGAT
   Consensus   (1551) AGAAAATGAGAGTGAGATATATCCAGATTTTGTGACGATTGCTAAAGGAT
```

FIG. 1 continued

```
               1601                                              1650
Shiloh8-Als1  (1601)  TCAACGTTCCAGCAGTTCGAGTGACGAAGAAGAGCGAAGTCACTGCAGCA
 Shiloh-Als1  (1601)  TCAACGTTCCAGCAGTTCGAGTGACGAAGAAGAGCGAAGTCACTGCAGCA
    Consensus (1601)  TCAACGTTCCAGCAGTTCGAGTGACGAAGAAGAGCGAAGTCACTGCAGCA 1651                                              1700
Shiloh8-Als1  (1651)  ATCAAGAAGATGCTTGAGACCCCAGGGCCATACTTGTTGGATATCATAGT
 Shiloh-Als1  (1651)  ATCAAGAAGATGCTTGAGACCCCAGGGCCATACTTGTTGGATATCATAGT
    Consensus (1651)  ATCAAGAAGATGCTTGAGACCCCAGGGCCATACTTGTTGGATATCATAGT 1701                                              1750
Shiloh8-Als1  (1701)  CCCGCATCAGGAGCACGTGCTGCCTATGATCCCAAGCGGTGGTGCTTTCA
 Shiloh-Als1  (1701)  CCCGCATCAGGAGCACGTGCTGCCTATGATCCCAAGCGGTGGTGCTTTCA
    Consensus (1701)  CCCGCATCAGGAGCACGTGCTGCCTATGATCCCAAGCGGTGGTGCTTTCA 1751                                1788
Shiloh8-Als1  (1751)  AGGACATGATCATGGAGGGTGATGGCAGGACCTCGTAC
 Shiloh-Als1  (1751)  AGGACATGATCATGGAGGGTGATGGCAGGACCTCGTAC
    Consensus (1751)  AGGACATGATCATGGAGGGTGATGGCAGGACCTCGTAC
```

FIG. 2

```
                        1                                                  50
Shiloh8_Als1    (1)  LPARIVRCCAASPAATSAAPPATALRPWGPSEPRKGADILVEALERCGIV
Shiloh_Als1     (1)  LPARIVRCCAASPAATSAAPPATALRPWGPSEPRKGADILVEALERCGIV
Consensus       (1)  LPARIVRCCAASPAATSAAPPATALRPWGPSEPRKGADILVEALERCGIV 51                                                100
Shiloh8_Als1   (51)  DVFAYPGGTSMEIHQALTRSPVITNHLFRHEQGEAFAASGYARASGRVGV
Shiloh_Als1    (51)  DVFAYPGGASMEIHQALTRSPVITNHLFRHEQGEAFAASGYARASGRVGV
Consensus      (51)  DVFAYPGG SMEIHQALTRSPVITNHLFRHEQGEAFAASGYARASGRVGV 101                                                150
Shiloh8_Als1  (101)  CVATSGPGATNLVSALADALLDSIPMVAITGQVPRRMIGTDAFQETPIVE
Shiloh_Als1   (101)  CVATSGPGATNLVSALADALLDSIPMVAITGQVPRRMIGTDAFQETPIVE
Consensus     (101)  CVATSGPGATNLVSALADALLDSIPMVAITGQVPRRMIGTDAFQETPIVE 151                                                200
Shiloh8_Als1  (151)  VTRSITKHNYLVLDVEDIPRVIQEAFFLASSGRPGPVLVDIPKDIQQQMA
Shiloh_Als1   (151)  VTRSITKHNYLVLDVEDIPRVIQEAFFLASSGRPGPVLVDIPKDIQQQMA
Consensus     (151)  VTRSITKHNYLVLDVEDIPRVIQEAFFLASSGRPGPVLVDIPKDIQQQMA 201                                                250
Shiloh8_Als1  (201)  VPVWDTPMSLPGYIARLPKPPSTESLEQVLRLVGESRRPILYVGGGCAAS
Shiloh_Als1   (201)  VPVWDTPMSLPGYIARLPKPPSTESLEQVLRLVGESRRPILYVGGGCAAS
Consensus     (201)  VPVWDTPMSLPGYIARLPKPPSTESLEQVLRLVGESRRPILYVGGGCAAS 251                                                300
Shiloh8_Als1  (251)  GEELRRFVELTGIPVTTTLMGLGNFPSDDPLSLRMLGMHGTVYANYAVDK
Shiloh_Als1   (251)  GEELRRFVELTGIPVTTTLMGLGNFPSDDPLSLRMLGMHGTVYANYAVDK
Consensus     (251)  GEELRRFVELTGIPVTTTLMGLGNFPSDDPLSLRMLGMHGTVYANYAVDK 301                                                350
Shiloh8_Als1  (301)  ADLLLAFGVRFDDRVTGKIEAFASRSKIVHIDIDPAEIGKNKQPHVSICA
Shiloh_Als1   (301)  ADLLLAFGVRFDDRVTGKIEAFASRSKIVHIDIDPAEIGKNKQPHVSICA
Consensus     (301)  ADLLLAFGVRFDDRVTGKIEAFASRSKIVHIDIDPAEIGKNKQPHVSICA 351                                                400
Shiloh8_Als1  (351)  DVKLALQGLNDLLNGSKAQQGLDFGPWHKELDQQKREFPLGFKTFGEAIP
Shiloh_Als1   (351)  DVKLALQGLNDLLNGSKAQQGLDFGPWHKELDQQKREFPLGFKTFGEAIP
Consensus     (351)  DVKLALQGLNDLLNGSKAQQGLDFGPWHKELDQQKREFPLGFKTFGEAIP 401                                                450
Shiloh8_Als1  (401)  PQYAIQVLDELTKGEAIIATGVGQHQMWAAQYYTYKRPRQWLSSSGLGAM
Shiloh_Als1   (401)  PQYAIQVLDELTKGEAIIATGVGQHQMWAAQYYTYKRPRQWLSSSGLGAM
Consensus     (401)  PQYAIQVLDELTKGEAIIATGVGQHQMWAAQYYTYKRPRQWLSSSGLGAM 451                                                500
Shiloh8_Als1  (451)  GFGLPAAAGAAVANPGVTVVDIDGDGSFLMNIQELALIRIENLPVKVMIL
Shiloh_Als1   (451)  GFGLPAAAGAAVANPGVTVVDIDGDGSFLMNIQELALIRIENLPVKVMIL
Consensus     (451)  GFGLPAAAGAAVANPGVTVVDIDGDGSFLMNIQELALIRIENLPVKVMIL
```

FIG. 2 continued

```
              501                                                550
Shiloh8_Als1  (501) NNQHLGMVVQWEDRFYKANRAHTYLGNPENESEIYPDFVTIAKGFNVPAV
 Shiloh_Als1  (501) NNQHLGMVVQWEDRFYKANRAHTYLGNPENESEIYPDFVTIAKGFNVPAV
    Consensus (501) NNQHLGMVVQWEDRFYKANRAHTYLGNPENESEIYPDFVTIAKGFNVPAV 551                                                600
Shiloh8_Als1  (551) RVTKKSEVTAAIKKMLETPGPYLLDIIVPHQEHVLPMIPSGGAFKDMIME
 Shiloh_Als1  (551) RVTKKSEVTAAIKKMLETPGPYLLDIIVPHQEHVLPMIPSGGAFKDMIME
    Consensus (551) RVTKKSEVTAAIKKMLETPGPYLLDIIVPHQEHVLPMIPSGGAFKDMIME 601
Shiloh8_Als1  (601) GDGRTSY
 Shiloh_Als1  (601) GDGRTSY
    Consensus (601) GDGRTSY
```

MUTATION INVOLVED IN INCREASED TOLERANCE TO IMIDAZOLINONE HERBICIDES IN PLANTS

CROSS-REFERENCE TO RELATED APPLICATIONS

This application is the U.S. National Stage of International Application PCT/US2005/043577 filed Dec. 1, 2005, which was published by the International Bureau in English on Jun. 8, 2006 and which claims the benefit of U.S. Provisional Application No. 60/632,376 filed Dec. 1, 2004; all of which are hereby incorporated herein in their entirety by reference.

FIELD OF THE INVENTION

The present invention relates in general to plants having an increased tolerance to imidazolinone herbicides. More specifically, the present invention relates to plants obtained by mutagenesis, cross-breeding, and transformation that have an increased tolerance to imidazolinone herbicides.

BACKGROUND OF THE INVENTION

Acetohydroxyacid synthase (AHAS; EC 4.1.3.18; acetolactate synthase (ALS)), encoded by the Als nucleic acid, is the first enzyme that catalyzes the biochemical synthesis of the branched chain amino acids valine, leucine, and isoleucine (Singh B. K., 1999, Biosynthesis of valine, leucine and isoleucine in: Singh B. K. (Ed) Plant amino acids. Marcel Dekker Inc. New York, N.Y. Pg 227-247). AHAS is the site of action of four structurally diverse herbicide families including the sulfonylureas (LaRossa R A and Falco S C, 1984, Trends Biotechnol. 2:158-161), the imidazolinones (Shaner et al., 1984, Plant Physiol. 76:545-546), the triazolopyrimidines (Subramanian and Gerwick, 1989, Inhibition of acetolactate synthase by triazolopyrimidines in (ed) Whitaker J R, Sonnet P E Biocatalysis in agricultural biotechnology. ACS Symposium Series, American Chemical Society. Washington, D.C. Pg 277-288), and the pyrimidyloxybenzoates (Subramanian et al., 1990, Plant Physiol. 94: 239-244). Imidazolinone and sulfonylurea herbicides are widely used in modern agriculture due to their effectiveness at very low application rates and relative non-toxicity in animals. By inhibiting AHAS activity, these families of herbicides prevent further growth and development of susceptible plants including many weed species. Several examples of commercially available imidazolinone herbicides are PURSUIT® (imazethapyr), SCEPTER® (imazaquin) and ARSENAL® (imazapyr). Examples of sulfonylurea herbicides are chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfuron, fluzasulfuron, imazosulfuron, pyrazosulfuron ethyl, and halosulfuron.

Due to their high effectiveness and low toxicity, imidazolinone herbicides are favored for application by spraying over the top of a wide area of vegetation. The ability to spray an herbicide over the top of a wide range of vegetation decreases the costs associated with plantation establishment and maintenance, and decreases the need for site preparation prior to use of such chemicals. Spraying over the top of a desired tolerant species also results in the ability to achieve maximum yield potential of the desired species due to the absence of competitive species. However, the ability to use such spray-over techniques is dependent upon the presence of imidazolinone tolerant species of the desired vegetation in the spray over area.

Among the major agricultural crops, some leguminous species such as soybean are naturally tolerant to imidazolinone herbicides due to their ability to rapidly metabolize the herbicide compounds (Shaner and Robson, 1985, Weed Sci. 33:469-471). Other crops such as corn (Newhouse et al., 1992, Plant Physiol. 100:882-886) and rice (Barrett et al., 1989, Crop Safeners for Herbicides, Academic Press New York, pp. 195-220) are susceptible to imidazolinone herbicides. The differential sensitivity to the imidazolinone herbicides is dependent on the chemical nature of the particular herbicide and differential metabolism of the compound from a toxic to a non-toxic form in each plant (Shaner et al., 1984, Plant Physiol. 76:545-546; Brown et al., 1987, Pestic. Biochem. Physiol. 27:24-29). Other plant physiological differences such as absorption and translocation also play an important role in sensitivity (Shaner and Robson, 1985, Weed Sci. 33:469-471).

Crop cultivars tolerant to imidazolinones, sulfonylureas, and triazolopyrimidines have been successfully produced using seed, microspore, pollen, and callus mutagenesis in *Zea mays, Brassica napus, Glycine max*, and *Nicotiana tabacum* (Sebastian et al., 1989, Crop Sci. 29:1403-1408; Swanson et al., 1989, Theor. Appl. Genet. 78:525-530; Newhouse et al., 1991, Theor. Appl. Genet. 83:65-70; Sathasivan et al., 1991, Plant Physiol. 97:1044-1050; Mourand et al., 1993, J. Heredity 84:91-96). In all cases, a single, partially dominant nuclear gene conferred tolerance. Four imidazolinone tolerant wheat plants were also previously isolated following seed mutagenesis of *Triticum aestivum* L. cv Fidel (Newhouse et al., 1992, Plant Physiol. 100:882-886). Inheritance studies confirmed that a single, partially dominant gene conferred tolerance. Based on allelic studies, the authors concluded that the mutations in the four identified lines were located at the same locus. One of the Fidel cultivar tolerance genes was designated FS-4 (Newhouse et al., 1992, Plant Physiol. 100:882-886).

Computer-based modeling of the three dimensional conformation of the AHAS-inhibitor complex predicts several amino acids in the proposed inhibitor binding pocket as sites where induced mutations would likely confer selective tolerance to imidazolinones (Ott et al., 1996, J. Mol. Biol. 263: 359-368). Tobacco plants produced with some of these rationally designed mutations in the proposed binding sites of the AHAS enzyme have in fact exhibited specific tolerance to a single class of herbicides (Ott et al., 1996, J. Mol. Biol. 263:359-368).

Plant tolerance to imidazolinone herbicides has also been reported in a number of patents. U.S. Pat. Nos. 4,761,373, 5,331,107, 5,304,732, 6,211,438, 6,211,439, and 6,222,100 generally describe the use of an altered Als nucleic acid to elicit herbicide tolerance in plants, and specifically disclose certain imidazolinone tolerant corn lines. U.S. Pat. No. 5,013,659 discloses plants exhibiting herbicide tolerance possessing mutations in at least one amino acid in one or more conserved regions. The mutations described therein encode either cross-tolerance for imidazolinones and sulfonylureas or sulfonylurea-specific tolerance, but imidazolinone-specific tolerance is not described. Additionally, U.S. Pat. No. 5,731,180 and U.S. Pat. No. 5,767,361 discuss an isolated gene having a single amino acid substitution in a wild-type monocot AHAS amino acid sequence that results in imidazolinone-specific tolerance.

To date, the prior art has not described mutations in the Als1 gene that confer increased tolerance to an imidazolinone herbicide other than the mutation in the FS-4 imidazolinone tolerant line. Nor has the prior art described imidazolinone tolerant wheat or triticale plants comprising at least one altered Als nucleic acid from a *Triticum aestivum* Shiloh cultivar. Therefore, what is needed in the art is the identification of additional mutations that confer tolerance to imidazolinone herbicides. What are also needed in the art are wheat plants and triticale plants having increased tolerance to herbicides such as imidazolinone and containing at least one altered Als nucleic acid. Also needed are methods for controlling weed growth in the vicinity of such wheat plants and triticale plants. These compositions and methods would allow for the use of spray over techniques when applying herbicides to areas containing wheat plants and triticale plants.

SUMMARY OF THE INVENTION

The present invention provides wheat plants comprising IMI nucleic acids, wherein the wheat plant has increased tolerance to an imidazolinone herbicide as compared to a wild-type plant. The wheat plants can contain one, two, three, or more IMI alleles. In one embodiment, the wheat plant comprises at least one IMI nucleic acid. In another embodiment, the at least one IMI nucleic acid is an Imi1 nucleic acid. In another embodiment, the at least one IMI nucleic acid comprises a *Triticuni aestivuin* IMI nucleic acid. In another embodiment, the at least one IMI nucleic acid comprises a Shiloh cultivar IMI nucleic acid. In yet another embodiment, the wheat plant comprises multiple IMI nucleic acids located on different genomes. In another embodiment, the multiple IMI nucleic acids comprise a *Triticum aestivum* Shiloh cultivar Imi1 nucleic acid. Preferably, the Shiloh cultivar Imi1 nucleic acid encodes a protein comprising a mutation in a conserved amino acid sequence selected from the group consisting of a Domain A, a Domain B, a Domain C, a Domain D, and a Domain E. More preferably, the mutation is in a conserved Domain C. Also provided are plant parts and plant seeds derived from the wheat plants described herein.

The present invention also provides triticale plants comprising IMI nucleic acids, wherein the triticale plant has increased tolerance to an imidazolinone herbicide as compared to a wild-type triticale plant. In one embodiment, the triticale plant comprises at least one IMI nucleic acid. In another embodiment, the at least one IMI nucleic acid is an Imi1 nucleic acid. In another embodiment, the at least one IMI nucleic acid comprises a *Triticum aestivum* Shiloh cultivar IMI nucleic acid. In another embodiment, the wheat plant comprises multiple IMI nucleic acids located on different genomes. In yet another embodiment, the multiple IMI nucleic acids comprise a Shiloh cultivar Imi1 nucleic acid. In another embodiment, the IMI nucleic acids encode proteins comprising a mutation in a conserved amino acid sequence selected from the group consisting of a Domain A, a Domain B, a Domain C, a Domain D, and a Domain E. More preferably, the mutation is in a conserved Domain C. Even more preferably, the mutation encodes a polypeptide having an alanine to threonine substitution at position 96 of the ALS polypeptide. Also provided are plant parts and plant seeds derived from the triticale plants described herein.

The IMI nucleic acids of the present invention can comprise a polynucleotide sequence selected from the group consisting of: a polynucleotide as defined in SEQ ID NO:1; a polynucleotide sequence encoding a polypeptide as defined in SEQ ID NO:2; a polynucleotide comprising at least 60 consecutive nucleotides of any of the aforementioned polynucleotides; and a polynucleotide complementary to any of the aforementioned polynucleotides.

The plants of the present invention can be transgenic or non-transgenic. An example of a non-transgenic wheat plant having increased tolerance to an imidazolinone herbicide is the wheat plant having an ATCC Patent Deposit Designation Number PTA-5625; or a mutant, recombinant, or genetically engineered derivative of the plant with ATCC Patent Deposit Designation Number PTA-5625; or any progeny of the plant with ATCC Patent Deposit Designation Number PTA-5625; or a plant that is a progeny of any of these plants.

In addition to the compositions of the present invention, several methods are provided. Described herein are methods of modifying a plant's tolerance to an imidazolinone herbicide comprising modifying the expression of an IMI nucleic acid in the plant. Also described are methods of producing a transgenic plant having increased tolerance to an imidazolinone herbicide comprising, transforming a plant cell with an expression vector comprising one or more IMI nucleic acids and generating the plant from the plant cell. The invention further includes a method of controlling weeds within the vicinity of a wheat or triticale plant, comprising applying an imidazolinone herbicide to the weeds and to the wheat or triticale plant, wherein the wheat or triticale plant has increased tolerance to the imidazolinone herbicide as compared to a wild type wheat or triticale plant and wherein the plant comprises one or more IMI nucleic acids. In some preferred embodiments of these methods, the plants comprise multiple IMI nucleic acids that are located on different wheat genomes.

Also provided are expression cassettes, transformation vectors, transformed non-human host cells, and transformed plants, plant cells, plant parts, and seeds that comprise one or more the IMI nucleic acids of the invention.

BRIEF DESCRIPTION OF THE DRAWINGS

FIG. 1 shows an alignment of the cDNA sequence of the Shiloh-8 Imi1 nucleic acid (SEQ ID NO:1), the wild type Als1 nucleic acid (SEQ ID NO:3), and a consensus nucleic acid sequence (SEQ ID NO:5). The base pair substituted in the Imi1 sequence is indicated in bold.

FIG. 2 shows an alignment of the deduced amino acid sequence of the Shiloh-8 IMI1 polypeptide (SEQ ID NO:2), a wild type ALS1 polypeptide (SEQ ID NO:4), and a consensus amino acid sequence (SEQ ID NO:6). The amino acid substituted in the IMI1 sequence is indicated in bold.

DETAILED DESCRIPTION

Figure 3:
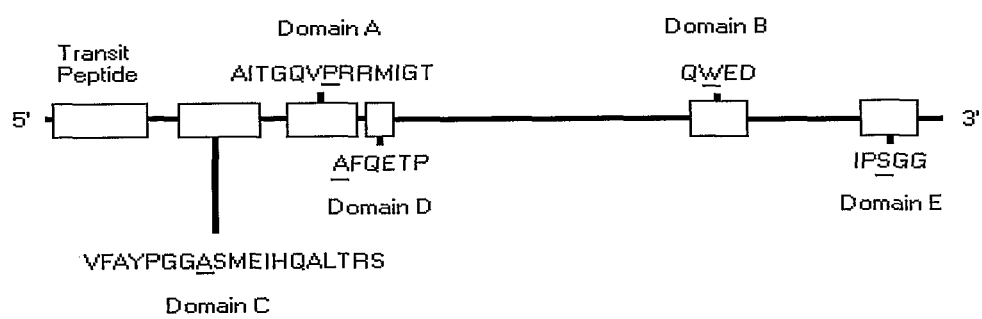
FIG. 3 is a schematic representation of the conserved amino acid sequences in the AHAS genes implicated in tolerance to various AHAS inhibitors. The specific amino acid site responsible for tolerance is indicated by an underline. (Modified from Devine, M. D. and Eberlein, C. V., 1997, Physiological, biochemical, and molecular aspects of herbicide tolerance based on altered target sites in Herbicide Activity: Toxicity, Biochemistry, and Molecular Biology, IOS Press Amersterdam, p. 159-185).

The present invention is directed to isolated nucleic acids encoding polypeptides that confer increased tolerance to an imidazolinone herbicide when expressed in a plant. The present invention is also directed to wheat or triticale plants, wheat or triticale plant parts, and wheat or triticale plant cells having increased tolerance to imidazolinone herbicides. The present invention also includes seeds produced by the wheat or triticale plants described herein and methods for controlling weeds in the vicinity of the wheat or triticale plants described herein.

As used herein, the term "wheat plant" refers to a plant that is a member of the *Triticum* genus. The wheat plants of the present invention can be members of a *Triticum* genus including, but not limited to, *T. aestivum, T. turgidum, T. timopheevii, T. monococcum, T. zhukovskyi*, and *T. urartu*, and hybrids thereof. Examples of *T. aestivum* subspecies included within the present invention are *aestivum* (common wheat), *compactum* (club wheat), *macha* (macha wheat), *vavilovi* (vavilovi wheat), *spelta* and *sphaecrococcum* (shot wheat). Examples of *T. turgidum* subspecies included within the present invention are *turgidum, carthlicum, dicoccom, durum, paleocolchicum, polonicum, turanicum*, and *dicoccoides*. Examples of *T. monococcum* subspecies included within the present invention are *monococcum* (einkorn) and *aegilopoides*. In one embodiment of the present invention, the wheat plant is a member of the *Triticum aestivuin* L. species, and more particularly, a Shiloh cultivar.

The term "wheat plant" is intended to encompass wheat plants at any stage of maturity or development, as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts, and the like. The present invention also includes seeds produced by the wheat plants of the present invention. In one embodiment, the seeds are true breeding for an increased tolerance to an imidazolinone herbicide as compared to a wild type wheat plant seed.

The present invention also encompasses triticale plants, triticale plant parts, and triticale plant cells having increased tolerance to imidazolinone herbicides. As used herein, a "triticale plant" refers to a plant that is created by crossing a rye plant (*Secale cereale*) with either a tetraploid wheat plant (e.g. *Triticuni turgidum*) or a hexaploid wheat plant (e.g. *Triticum aestivum*). The present invention also includes seeds produced by the triticale plants described herein and methods for controlling weeds in the vicinity of the triticale plants described herein.

The present invention describes a wheat plant comprising at least one IMI nucleic acid, wherein the wheat plant has increased tolerance to an imidazolinone herbicide as compared to a wild-type plant. It is possible for the wheat plants of the present invention to have multiple IMI nucleic acids from different genomes since these plants can contain more than one genome. For example, a *Triticuni aestivum* wheat plant contains three genomes referred to as the A, B, and D genomes. Because AHAS is a required metabolic enzyme, it is assumed that each genome has at least one gene coding for the AHAS enzyme (i.e. at least one Als gene), commonly seen with other metabolic enzymes in hexaploid wheat that have been mapped. As used herein, the term "Als gene locus" refers to the position of an Als gene on a genome, and the terms "Als gene" and "Als nucleic acid" refer to a nucleic acid encoding the AHAS enzyme. The Als nucleic acid on each genome differs in its nucleotide sequence from an Als nucleic acid on another genome. One of skill in the art can determine the genome of origin of each Als nucleic acid through genetic crossing and/or either sequencing methods or exonuclease digestion methods known to those of skill in the art. As used herein, the terms "Als1 nucleic acid," "Als2 nucleic acid," and "Als3 nucleic acid" refer to Als nucleic acids located on three different genomes. For the purposes of this invention, the Als3 gene locus is located on the A genome, the Als2 gene locus is located on the B genome, and the Als1 gene locus is located on the D genome. Also for the purposes of this invention, IMI nucleic acids derived from the A, B, or D genomes are distinguished and designated as Imi3, Imi2, or Imi1 nucleic acids, respectively.

As used herein, the term "IMI nucleic acid" refers to an Als nucleic acid having a sequence that is mutated from a wild type Als nucleic acid and that confers increased imidazolinone tolerance to a plant in which it is expressed. As used herein, the terms "Imi1 nucleic acid," "Imi2 nucleic acid," and "Imi3 nucleic acid" are IMI nucleic acids that refer to the imidazolinone tolerance alleles of the Als1, Als2, and Als3 genes, respectively. Because wheat plants have two copies of each genome, a wheat plant contains two copies of each particular Als nucleic acid. For example, a *Triticum aestivum* wheat plant comprises two copies each of the A, B, and D genomes, and therefore, two copies each of the Als3, Als2, and Als1 genes. As used herein, the term "IMI allele" refers to a single copy of a particular IMI nucleic acid. Accordingly, for the purposes of the present invention, a wheat plant may have two Imi1 alleles, one on each of two copies of the D genome.

In another embodiment, the wheat plant comprises multiple IMI nucleic acids. As used herein, when describing a plant that comprises "multiple IMI nucleic acids," the phrase "multiple IMI nucleic acids" refers to the presence of different IMI nucleic acids in the plant and not to whether the plant is homozygous or heterozygous at a particular Als locus. For example, a plant comprising multiple IMI nucleic acids may comprise an Imi1 and an Imi2 nucleic acid, as opposed to having two copies of an Imi1 nucleic acid.

The Imi1 class of nucleic acids includes the FS-4 gene as described by Newhouse et al. (1992 Plant Physiol. 100:882-886) and the Shiloh-8 gene described in more detail below. Each Imi class can include members from different wheat species. Therefore, each Imi class includes IMI nucleic acids that differ in their nucleotide sequence but that are nevertheless designated as originating from, or being located on, the same wheat genome using inheritance studies as known to those of ordinary skill in the art.

Accordingly, the present invention includes a wheat plant comprising at least one IMI nucleic acid, wherein the wheat plant has increased tolerance to an imidazolinone herbicide as compared to a wild-type plant and wherein the at least one IMI nucleic acid is an Imi1 nucleic acid. In a preferred embodiment, the Imi1 nucleic acid comprises the polynucleotide sequence shown in SEQ ID NO:1. In another preferred embodiment, the wheat plant comprises multiple IMI nucleic acids.

The present invention also encompasses an imidazolinone tolerant triticale plant. As used herein, a "triticale plant" refers to a plant that is created by crossing a rye plant (*Secale cereale*) with either a tetraploid wheat plant (e.g. *Triticum turgidum*) or a hexaploid wheat plant (e.g. *Triticum aestivum*). For the purposes of the present invention, an imidazolinone tolerant triticale plant comprises at least one IMI nucleic acid, wherein the triticale plant has increased tolerance to an imidazolinone herbicide as compared to a wild-type plant and wherein the at least one IMI nucleic acid is an Imi1 nucleic acid. In a preferred embodiment, the Imi1 nucleic acid comprises the polynucleotide sequence of SEQ ID NO:1. In another preferred embodiment, the triticale plant comprises multiple IMI nucleic acids.

As used herein with regard to nucleic acids, the term "from" refers to a nucleic acid "located on" or "derived from" a particular genome. The term "located on" refers to a nucleic acid contained within that particular genome. As also used herein with regard to a genome, the term "derived from"

refers to a nucleic acid that has been removed or isolated from that genome. The term "isolated" is defined in more detail below.

The present invention includes wheat plants comprising one, two, three, or more IMI alleles, wherein the wheat plant has increased tolerance to an imidazolinone herbicide as compared to a wild-type plant. The IMI alleles can comprise a nucleotide sequence selected from the group consisting of a polynucleotide as defined in SEQ ID NO:1; a polynucleotide encoding a polypeptide as defined in SEQ ID NO:2; a polynucleotide comprising at least 60 consecutive nucleotides of any of the aforementioned polynucleotides; and a polynucleotide complementary to any of the aforementioned polynucleotides.

The present invention also includes triticale plants comprising one, two, three, or more IMI alleles, wherein the triticale plant has increased tolerance to an imidazolinone herbicide as compared to a wild-type plant. The IMI alleles can comprise a polynucleotide sequence selected from the group consisting of a polynucleotide as defined in SEQ ID NO:1; a polynucleotide encoding a polypeptide as defined in SEQ ID NO:2; a polynucleotide comprising at least 60 consecutive nucleotides of any of the aforementioned polynucleotides; and a polynucleotide complementary to any of the aforementioned polynucleotides.

In one embodiment, the wheat plant or triticale plant comprises two different IMI nucleic acids. Preferably, at least one of the two nucleic acids is an Imi1 nucleic acid. More preferably, at least one of the two IMI nucleic acids comprises the polynucleotide sequence of SEQ ID NO:1. In another embodiment, the wheat plant or triticale plant comprises one IMI nucleic acid, wherein the nucleic acid comprises the polynucleotide sequence of SEQ ID NO:1. In yet another embodiment, the wheat plant comprises greater than two IMI nucleic acids wherein each IMI nucleic acid is from a different genome. Preferably, at least one of the IMI nucleic acids comprises a polynucleotide sequence encoding the polypeptide sequence of SEQ ID NO:2, or the polynucleotide sequence of SEQ ID NO:1.

In a preferred embodiment of the present invention, the isolated IMI nucleic acid encodes an amino acid sequence comprising a mutation in a domain that is conserved among several AHAS proteins. These conserved domains are referred to herein as Domain A, Domain B, Domain C, Domain D, and Domain E. FIG. 3 shows the general location of each domain in an AHAS protein. Domain A contains the amino acid sequence AITGQVPRRMIGT (SEQ ID NO:7). Domain B contains the amino acid sequence QWED (SEQ ID NO:8). Domain C contains the amino acid sequence VFAYPGGASMEIHQALTRS (SEQ ID NO:9). Domain D contains the amino acid sequence AFQETP (SEQ ID NO:10). Domain E contains the amino acid sequence IPSGG (SEQ ID NO:11). The present invention also contemplates that there may be slight variations in the conserved domains, for example, in cockleber plants, the serine residue in Domain E is replaced by an alanine residue.

Accordingly, the present invention includes a wheat plant or triticale plant comprising an IMI nucleic acid that encodes an amino acid sequence having a mutation in a conserved domain selected from the group consisting of a Domain A, a Domain B, a Domain C, a Domain D, and a Domain E. In one embodiment, the wheat plant or triticale plant comprises an IMI nucleic acid that encodes an amino acid sequence having a mutation in a Domain E. In further preferred embodiments, the mutations in the conserved domains occur at the locations indicated by the following underlining: AITGQVPRRMIGT (SEQ ID NO:7); QWED (SEQ ID NO:8); VFAYPGG ASMEIHQALTRS (SEQ ID NO:9); AFQETP (SEQ ID NO:10), and IPSGG (SEQ ID NO:11). One preferred substitution is an alanine to threonine in Domain C. Even more preferably, the substitution is an alanine to threonine substitution at position 96 of the ALS polypeptide.

The present invention provides methods for enhancing the tolerance or resistance of a plant, plant tissue, plant cell, or other host cell to at least one herbicide that interferes with the activity of the AHAS enzyme. The present invention further provides plants, plant cells, plant parts, plant organs, plant tissues, seeds, and host cells with tolerance to at least one herbicide, particularly an AHAS-inhibiting herbicide. Preferably, such an AHAS-inhibiting herbicide is an imidazolinone herbicide, a sulfonylurea herbicide, a triazolopyrimidine herbicide, a pyrimidinyloxybenzoate herbicide, a sulfonylamino-carbonyltriazolinone herbicide, or mixture thereof. More preferably, such a herbicide is an imidazolinone herbicide or mixture of two or more imidazolinone herbicides. For the present invention, the imidazolinone herbicides include, but are not limited to, PURSUIT® (imazethapyr), CADRE® (imazapic), RAPTOR® (imazamox), SCEPTER® (imazaquin), ASSERT® (imazethabenz), ARSENAL® (imazapyr), a derivative of any of the aforementioned herbicides, and a mixture of two or more of the aforementioned herbicides, for example, imazapyr/imazamox (ODYSSEY®). More specifically, the imidazolinone herbicide can be selected from, but is not limited to, 2-(4-isopropyl-4-methyl-5-oxo-2-imidiazolin-2-yl)-nicotinic acid, [2-(4-isopropyl)-4-][methyl-5-oxo-2-imidazolin-2-yl)-3-quinolinecarboxylic] acid, [5-ethyl-2-(4-isopropyl-]-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, [2-(4-isopropyl-4-methyl-5-oxo-2-]imidazolin-2-yl)-5-methylnicotinic acid, and a mixture of methyl [6-(4-isopropyl-4-]methyl-5-oxo-2-imidazolin-2-yl)-m-toluate and methyl [2-(4-isopropyl-4-methyl-5-]oxo-2-imidazolin-2-yl)-p-toluate. The use of 5-ethyl-2-(4-isopropyl-4-methyl-5-oxo-2-imidazolin-2-yl)-nicotinic acid and [2-(4-isopropyl-4-methyl-5-oxo-2-imidazolin-2-]yl)-5-(methoxymethyl)-nicotinic acid is preferred. The use of [2-(4-isopropyl-4-]methyl-5-oxo-2-imidazolin-2-yl)-5-(methoxymethyl)-nicotinic acid is particularly preferred.

For the present invention, the sulfonylurea herbicides include, but are not limited to, chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfuron, fluzasulfuron, imazosulfuron, pyrazosulfuron ethyl, halosulfuron, azimsulfuron, cyclosulfuron, ethoxysulfuron, flazasulfuron, flupyrsulfuron methyl, foramsulfuron, iodosulfuron, oxasulfuron, mesosulfuron, prosulfuron, sulfosulfuron, trifloxysulfuron, tritosulfuron, a derivative of any of the aforementioned herbicides, and a mixture of two or more of the aforementioned herbicides. The triazolopyrimidine herbicides of the invention include, but are not limited to, cloransulam, diclosulam, florasulam, flumetsulam, metosulam, and penoxsulam. The pyrimidinyloxybenzoate herbicides of the invention include, but are not limited to, bispyribac, pyrithiobac, pyriminobac, pyribenzoxim and pyriftalid. The sulfonylamino-carbonyltriazolinone herbicides include, but are not limited to, flucarbazone and propoxycarbazone.

It is recognized that pyrimidinyloxybenzoate herbicides are closely related to the pyrimidinylthiobenzoate herbicides and are generalized under the heading of the latter name by the Weed Science Society of America. Accordingly, the herbicides of the present invention further include pyrimidinylthiobenzoate herbicides, including, but not limited to, the pyrimidinyloxybenzoate herbicides described above.

The wheat plants described herein can be either transgenic wheat plants or non-transgenic wheat plants. Similarly, the triticale plants described herein can be either transgenic triticale plants or non-transgenic triticale plants. As used herein, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding. Plants containing mutations arising due to non-spontaneous mutagenesis and selective breeding are referred to herein as non-transgenic plants and are included in the present invention. In embodiments wherein the wheat plant or triticale plant is transgenic and comprises multiple IMI nucleic acids, the nucleic acids can be derived from different genomes or from the same genome. Alternatively, in embodiments wherein the wheat plant or triticale plant is non-transgenic and comprises multiple IMI nucleic acids, the nucleic acids are located on different genomes or on the same genome.

An example of a non-transgenic wheat plant cultivar comprising one IMI nucleic acid is the plant cultivar deposited with the ATCC under Patent Deposit Designation Number PTA-5625 and designated herein as the Shiloh-8 line. The Shiloh-8 line contains an Imi1 nucleic acid. The partial-length nucleotide sequence corresponding to the Shiloh-8 gene is shown in SEQ ID NO:1.

A deposit of 2500 seeds of the Shiloh-8 line (designated i4417-8) was made with the American Type Culture Collection, Manassas, Va. on Oct. 30, 2003. These deposits were made in accordance with the terms and provisions of the Budapest Treaty relating to the deposit of microorganisms. The deposits were made for a term of at least thirty years and at least five years after the most recent request for the furnishing of a sample of the deposit is received by the ATCC. The deposited seeds were accorded Patent Deposit Designation Number PTA-5625.

The present invention includes the wheat plant having a Patent Deposit Designation Number PTA-5625; a mutant, recombinant, or genetically engineered derivative of the plant with Patent Deposit Designation Number PTA-5625; any progeny of the plant with Patent Deposit Designation Number PTA-5625; and a plant that is the progeny of any of these plants. In a preferred embodiment, the wheat plant of the present invention additionally has the herbicide tolerance characteristics of the plant with Patent Deposit Designation Number PTA-5625.

Also included in the present invention are hybrids of the Shiloh-8 wheat plants described herein and hybrids of the Shiloh-8 with another wheat plant. The other wheat plant includes, but is not limited to, *T. aestivum* L. cv Fidel and any wheat plant harboring a mutant gene FS-1, FS-2, FS-3 or FS-4. (See U.S. Pat. No. 6,339,184 and U.S. patent application Ser. No. 08/474,832).

The terms "cultivar" and "variety" refer to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. The terms "breeding line" or "line" refer to a group of plants within a cultivar defined by the sharing of a common set of characteristics or traits accepted by those skilled in the art as sufficient to distinguish one breeding line or line from another breeding line or line. There is no implication in either term that all plants of any given breeding line or line will be genetically identical at either the whole gene or molecular level or that any given plant will be homozygous at all loci. A breeding line or line is considered "true breeding" for a particular trait if, when the true-breeding line or breeding line is self-pollinated, all of the progeny contain the trait. In the present invention, the trait arises from a mutation in an Als gene of the wheat or triticale plant or seed.

Furthermore, the use of the terms "cultivar" and "variety" herein is not intended to limit the plants of the present invention to one or more plant varieties. While the present invention encompasses plant varieties, the plants of the present invention include any plants that comprise the herbicide-tolerance characteristics of the plant of ATCC Patent Deposit Number 5625 and/or one or more of the IMI nucleic acids of the present invention.

It is to be understood that the wheat or triticale plant of the present invention can comprise a wild type Als nucleic acid in addition to an IMI nucleic acid. As described in Example 1, it is contemplated that the Shiloh-8 line contains a mutation in only one of multiple AHAS isoenzymes. Therefore, the present invention includes a wheat plant or triticale plant comprising at least one IMI nucleic acid in addition to one or more wild type Als nucleic acids.

In addition to wheat and triticale plants, the present invention encompasses isolated IMI proteins and nucleic acids. The nucleic acids comprise a polynucleotide selected from the group consisting of a polynucleotide as defined in SEQ ID NO:1; a polynucleotide encoding of a polypeptide as defined in SEQ ID NO:2; a polynucleotide comprising at least 60 consecutive nucleotides of any of the aforementioned polynucleotides; and a polynucleotide complementary to any of the aforementioned polynucleotides. In a preferred embodiment, the IMI nucleic acid comprises a polynucleotide sequence of SEQ ID NO:1.

The terms "AHAS protein," "AHAS polypeptide," "ALS protein," and "ALS polypeptide" refer to an acetohydroxy-acid synthase protein, and the terms "IMI protein" or "IMI polypeptide" refer to any AHAS protein that is mutated from a wild type AHAS protein and that confers increased imidazolinone tolerance to a plant, plant cell, plant part, plant seed, or plant tissue when it is expressed therein. In a preferred embodiment, the IMI protein comprises a polypeptide encoded by a polynucleotide sequence comprising SEQ ID NO:1. Such IMI proteins comprise herbicide-tolerant AHAS activity, particularly imidazolinone-tolerant AHAS activity. Such herbicide-tolerant AHAS activity can be evaluated by AHAS activity assays. See, for example, Singh et al. (1988) *Anal. Biochem.* 171:173-179, herein incorporated by reference.

In another preferred embodiment, the IMI protein comprises a polypeptide comprising SEQ ID NO:2. As also used herein, the terms "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences that naturally flank the nucleic acid (i.e., sequences located at the 5' and 3' ends of the nucleic acid) in its naturally occurring replicon. For example, a cloned nucleic acid is considered isolated. In various embodiments, the isolated IMI nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a *Triticum aestivum* cell). A nucleic acid is also considered isolated if it has been altered by human intervention, or placed in a locus or location that is not its natural site, or if it is introduced into a cell by agroinfection, biolistics, or any other method of plant transformation. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule containing a nucleotide sequence of SEQ ID NO:1 or a portion thereof, can be isolated using standard molecular biology techniques and the sequence information provided herein. For example, a *T. aestivum* IMI cDNA can be isolated from a *T. aestivum* library using all or a portion of the sequence of SEQ ID NO:1. Moreover, a nucleic acid molecule encompassing all or a portion of SEQ ID NO:1 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979, Biochemistry 18:5294-5299), and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon the nucleotide sequence shown in SEQ ID NO:1. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to an IMI nucleotide sequence can be prepared by standard synthetic techniques, e.g., using an automated DNA synthesizer.

The IMI nucleic acids of the present invention can comprise sequences encoding an IMI protein (i.e., "coding regions"), as well as 5' untranslated sequences and 3' untranslated sequences. Alternatively, the nucleic acid molecules of the present invention can comprise only the coding regions of an IMI gene, or can contain whole genomic fragments isolated from genomic DNA. A coding region of these sequences is indicated as an "ORF position." Moreover, the nucleic acid molecule of the invention can comprise a portion of a coding region of an IMI gene, for example, a fragment that can be used as a probe or primer. The nucleotide sequences determined from the cloning of the IMI genes from *T. aestivum* allow for the generation of probes and primers designed for use in identifying and/or cloning IMI homologs in other cell types and organisms, as well as IMI homologs from other wheat plants and related species. The portion of the coding region can also encode a biologically active fragment of an IMI protein.

As used herein, the term "biologically active portion of" an IMI protein is intended to include a portion, e.g., a domain/motif, of an IMI protein that, when produced in a plant increases the plant's tolerance to an imidazolinone herbicide as compared to a wild-type plant. Methods for quantitating increased tolerance to imidazolinone herbicides are provided in the Examples below. Biologically active portions of an IMI protein include peptides derived from SEQ ID NO:2 which include fewer amino acids than a fall length IMI protein and impart increased tolerance to an imidazolinone herbicide upon expression in a plant. Typically, biologically active portions (e.g., peptides which are, for example, 5, 10, 15, 20, 30, 35, 36, 37, 38, 39, 40, 50, 100, or more amino acids in length) comprise a domain or motif with at least one activity of an IMI protein. Moreover, other biologically active portions in which other regions of the polypeptide are deleted, can be prepared by recombinant techniques and evaluated for one or more of the activities described herein. Preferably, the biologically active portions of an IMI protein include one or more conserved domains selected from the group consisting of a Domain A, a Domain B, a Domain C, a Domain D and a Domain E, wherein the conserved domain contains a mutation.

The invention also provides IMI chimeric or fusion polypeptides. As used herein, an IMI "chimeric polypeptide" or "fusion polypeptide" comprises an IMI polypeptide operatively linked to a non-IMI polypeptide. A "non-IMI polypeptide" refers to a polypeptide having an amino acid sequence that is not substantially identical to an IMI polypeptide, e.g., a polypeptide that is not an IMI isoenzyme, which peptide performs a different function than an IMI polypeptide. As used herein with respect to the fusion polypeptide, the term "operatively linked" is intended to indicate that the IMI polypeptide and the non-IMI polypeptide are fused to each other so that both sequences fulfill the proposed function attributed to the sequence used. The non-IMI polypeptide can be fused to the N-terminus or C-terminus of the IMI polypeptide. For example, in one embodiment, the fusion polypeptide is a GST-IMI fusion polypeptide in which the IMI sequence is fused to the C-terminus of the GST sequence. Such fusion polypeptides can facilitate the purification of recombinant IMI polypeptides. In another embodiment, the fusion polypeptide is an IMI polypeptide containing a heterologous signal sequence at its N-terminus. In certain host cells (e.g., mammalian host cells), expression and/or secretion of an IMI polypeptide can be increased through use of a heterologous signal sequence.

An isolated nucleic acid molecule encoding an IMI polypeptide having a certain percent sequence identity to a polypeptide of SEQ ID NO:2 can be created by introducing one or more nucleotide substitutions, additions, or deletions into a nucleotide sequence of SEQ ID NO:1 such that one or more amino acid substitutions, additions, or deletions are introduced into the encoded polypeptide. Mutations can be introduced into a sequence of SEQ ID NO:1 by standard techniques, such as site-directed mutagenesis and PCR-mediated mutagenesis. Preferably, conservative amino acid substitutions are made at one or more predicted non-essential amino acid residues.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in an IMI polypeptide is preferably replaced with another amino acid residue from the same side chain family. Alternatively, in another embodiment, mutations can be introduced randomly along all or part of an IMI coding sequence, such as by saturation mutagenesis, and the resultant mutants can be screened for an IMI activity described herein to identify mutants that retain IMI activity. Following mutagenesis of the sequence of SEQ ID NO:1, the encoded polypeptide can be expressed recombinantly and the activity of the polypeptide can be determined by analyzing the imidazolinone tolerance of a plant expressing the polypeptide as described in the Examples below.

To determine the percent sequence identity of two amino acid sequences, the sequences are aligned for optimal comparison purposes (e.g., gaps can be introduced in the sequence of one polypeptide for optimal alignment with the other polypeptide). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences. The percent sequence identity between the two sequences is a function of the number of identical positions shared by the sequences (i.e., percent sequence identity=numbers of identical positions/total numbers of positions×100). For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings.

It is to be understood that for the purposes of determining sequence identity, when comparing a DNA sequence to an RNA sequence, a thymidine nucleotide is equivalent to a uracil nucleotide. Preferably, the isolated IMI nucleic acids of the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to the entire polynucleotide sequence shown in SEQ ID NO:1. In another embodiment, the isolated IMI nucleic acids included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire polynucleotide sequence shown in SEQ ID NO:1.

Preferably, the isolated IMI polypeptides of the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO:2. In another embodiment, the isolated IMI polypeptides included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO:2.

Additionally, optimized IMI nucleic acids can be created. Preferably, an optimized IMI nucleic acid encodes an IMI polypeptide that modulates a plant's tolerance to imidazolinone herbicides, and more preferably increases a plant's tolerance to an imidazolinone herbicide upon its overexpression in the plant. As used herein, "optimized" refers to a nucleic acid that is genetically engineered to increase its expression in a given plant or animal. To provide plant optimized IMI nucleic acids, the DNA sequence of the gene can be modified to 1) comprise codons preferred by highly expressed plant genes; 2) comprise an A+T content in nucleotide base composition to that substantially found in plants; 3) form a plant initiation sequence, 4) eliminate sequences that cause destabilization, inappropriate polyadenylation, degradation and termination of RNA, or that form secondary structure hairpins or RNA splice sites. Increased expression of IMI nucleic acids in plants can be achieved by utilizing the distribution frequency of codon usage in plants in general or a particular plant. Methods for optimizing nucleic acid expression in plants can be found in EPA 0359472; EPA 0385962; PCT Application No. WO 91/16432; U.S. Pat. No. 5,380,831; U.S. Pat. No. 5,436,391; Perlack et al., 1991, Proc. Natl. Acad. Sci. USA 88:3324-3328; and Murray et al., 1989, Nucleic Acids Res. 17:477-498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A=n=1\ Z\ X_n-Y_n\ X_n$ times $100\ Z$ where $X_n$=frequency of usage for codon n in the host cell; $Y_n$=frequency of usage for codon n in the synthetic gene, n represents an individual codon that specifies an amino acid and the total number of codons is Z. The overall deviation of the frequency of codon usage, A, for all amino acids should preferably be less than about 25%, and more preferably less than about 10%.

Hence, an IMI nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized IMI nucleic acids of this invention also preferably have CG and TA doublet avoidance indices closely approximating those of the chosen host plant (i.e., *Triticum aestivum*). More preferably these indices deviate from that of the host by no more than about 10-15%.

In addition to the nucleic acid molecules encoding the IMI polypeptides described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation and/or stability of the target polynucleotide. Methods are described in the prior art for targeting the antisense polynucleotide to the chromosomal DNA, to a primary RNA transcript or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide sequence of SEQ ID NO:2.

In addition to the IMI nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of the sequence set forth in SEQ ID NO:1, an anti-sense sequence of the sequence set forth in SEQ ID NO:1, or naturally occurring mutants thereof. Primers based on a nucleotide sequence of SEQ ID NO:1 can be used in PCR reactions to clone IMI homologs. Probes based on the IMI nucleotide sequences can be used to detect transcripts or genomic sequences encoding the same or homologous polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an IMI polypeptide, such as by measuring a level of an IMI-encoding nucleic acid, in a sample of cells, e.g., detecting IMI mRNA levels or determining whether a genomic IMI gene has been mutated or deleted.

The invention further provides an isolated recombinant expression vector comprising an IMI nucleic acid as described above, wherein expression of the vector in a host cell results in increased tolerance to an imidazolinone herbicide as compared to a wild type host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. With respect to a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., IMI polypeptides, fusion polypeptides, etc.).

In a preferred embodiment of the present invention, the IMI polypeptides are expressed in plants and plants cells such as unicellular plant cells (such as algae) (See Falciatore et al., 1999, Marine Biotechnology 1(3):239-251 and references therein) and plant cells from higher plants (e.g., the spermatophytes, such as crop plants). An IMI polynucleotide may be "introduced" into a plant cell by any means, including transfection, transformation or transduction, electroporation, particle bombardment, agroinfection, biolistics, and the like.

Suitable methods for transforming or transfecting host cells including plant cells can be found in Sambrook et al. (Molecular Cloning: A Laboratory Manual. $2^{nd}$, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, Agrobacterium protocols, ed: Gartland and Davey, Humana Press, Totowa, N.J. As increased tolerance to imidazolinone herbicides is a general trait wished to be inherited into a wide number of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses, and forage crops, these plants are also preferred target plants for a genetic engineering as one further embodiment of the present invention. In a preferred embodiment, the plant is a wheat plant. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of an IMI polynucleotide into a plant is achieved by Agrobacterium mediated gene transfer. One transformation method known to those of skill in the art is the dipping of a flowering plant into an Agrobacteria solution, wherein the Agrobacteria contains the IMI nucleic acid, followed by breeding of the transformed gametes. Agrobacterium mediated plant transformation can be performed using for example the GV3101 (pMP90) (Koncz and Schell, 1986, Mol. Gen. Genet. 204: 383-396) or LBA4404 (Clontech) Agrobacterium tumefaciens strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, $2^{nd}$ Ed.—Dordrecht: Kluwer Academic Publ., 1995,—in Sect., Ringbuc Zentrale Signatur: BT11-P ISBN 0-7923-2731-4; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for Agrobacterium and plant selection depends on the binary vector and the Agrobacterium strain used for transformation. Rapeseed selection is normally performed using kanamycin as selectable plant marker. Agrobacterium mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced IMI polynucleotide may be maintained in the plant cell stably if it is incorporated into a non-chromosomal autonomous replicon or integrated into the plant chromosomes. Alternatively, the introduced IMI polynucleotide may be present on an extra-chromosomal non-replicating vector and be transiently expressed or transiently active. In one embodiment, a homologous recombinant microorganism can be created wherein the IMI polynucleotide is integrated into a chromosome, a vector is prepared which contains at least a portion of an AHAS gene into which a deletion, addition or substitution has been introduced to thereby alter, e.g., functionally disrupt, the endogenous AHAS gene and to create an IMI gene. To create a point mutation via homologous recombination, DNA-RNA hybrids can be used in a technique known as chimeraplasty (Cole-Strauss et al., 1999, Nucleic Acids Research 27(5):1323-1330 and Kmiec, 1999, Gene therapy American Scientist 87(3):240-247). Other homologous recombination procedures in Triticum species are also well known in the art and are contemplated for use herein.

In the homologous recombination vector, the IMI gene can be flanked at its 5' and 3' ends by an additional nucleic acid molecule of the AHAS gene to allow for homologous recombination to occur between the exogenous IMI gene carried by the vector and an endogenous AHAS gene, in a microorganism or plant. The additional flanking AHAS nucleic acid molecule is of sufficient length for successful homologous recombination with the endogenous gene. Typically, several hundreds of base pairs up to kilobases of flanking DNA (both at the 5' and 3' ends) are included in the vector (See, e.g., Thomas, K. R., and Capecchi, M. R., 1987, Cell 51:503 for a description of homologous recombination vectors or Strepp et al., 1998, PNAS, 95(8):4368-4373 for cDNA based recombination in *Physcomitrella patens*). However, since the IMI gene normally differs from the AHAS gene at very few amino acids, a flanking sequence is not always necessary. The homologous recombination vector is introduced into a microorganism or plant cell (e.g., via polyethylene glycol mediated DNA), and cells in which the introduced IMI gene has homologously recombined with the endogenous AHAS gene are selected using art-known techniques.

In another embodiment, recombinant microorganisms can be produced that contain selected systems that allow for regulated expression of the introduced gene. For example, inclusion of an IMI gene on a vector placing it under control of the lac operon permits expression of the IMI gene only in the presence of IPTG. Such regulatory systems are well known in the art.

Whether present in an extra-chromosomal non-replicating vector or a vector that is integrated into a chromosome, the IMI polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

Plant gene expression should be operatively linked to an appropriate promoter conferring gene expression in a timely, cell type-preferred, or tissue-preferred manner. Promoters useful in the expression cassettes of the invention include any promoter that is capable of initiating transcription in a plant cell. Such promoters include, but are not limited to those that can be obtained from plants, plant viruses and bacteria that contain genes that are expressed in plants, such as *Agrobacterium* and *Rhizobium*.

The promoter may be constitutive, inducible, developmental stage-preferred, cell type-preferred, tissue-preferred or organ-preferred. Constitutive promoters are active under most conditions. Examples of constitutive promoters include the CaMV 19S and 35S promoters (Odell et al., 1985, Nature 313:810-812), the sX CaMV 35S promoter (Kay et al., 1987, Science 236:1299-1302) the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and the like.

Inducible promoters are active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoter from tobacco, *Arabidopsis*, and maize are inducible by infection with a pathogen; and the Adh1 promoter is induced by hypoxia and cold stress. Plant gene expression can also be facilitated via an inducible promoter (For review, see Gatz, 1997, Annu. Rev. Plant Physiol. Plant Mol. Biol. 48:89-108). Chemically inducible promoters are especially suitable if time-specific gene expression is desired. Examples of such promoters are a salicylic acid inducible promoter (PCT Application No. WO 95/19443), a tetracycline inducible promoter (Gatz et al., 1992, Plant J. 2:397-404) and an ethanol inducible promoter (PCT Application No. WO 93/21334).

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed preferred promoters are preferentially expressed during seed development and/or germination. For example, seed preferred promoters can be embryo-preferred, endosperm preferred, and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1), and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991, Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2): 233-9), as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, *Sorghum* kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, Cell 43:729-736).

The present invention provides expression cassettes for expressing the polynucleotide molecules of the invention in plants, plant cells, and other, non-human host cells. The expression cassettes comprise a promoter expressible in the plant, plant cell, or other host cells of interest operably linked to an IMI nucleic acid. If necessary for targeting expression to the chloroplast, the expression cassette can also comprise an operably linked chloroplast-targeting sequence that encodes of a chloroplast transit peptide to direct an expressed IMI protein to the chloroplast.

In one embodiment, the IMI nucleic acids are targeted to the chloroplast for expression. In this manner, where the IMI nucleic acid is not directly inserted into the chloroplast, the expression cassette will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the IMI nucleic acid of the invention such that the two sequences are contiguous and in the same reading frame. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481. While the IMI proteins of the invention can include a native chloroplast transit peptide, any chloroplast transit peptide known in art can be fused to the amino acid sequence of a mature IMI protein of the invention by operably linking a chloroplast-targeting sequence to the 5'-end of a nucleotide sequence encoding a mature IMI protein of the invention.

Chloroplast targeting sequences are known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6):789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36):27447-27457); and the light harvesting chlorophyll a/b binding protein (LHBP) (Lamppa et al. (1988) *J. Biol. Chem.* 263:14996-14999). See also Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The IMI nucleic acids or expression cassettes comprising the IMI nucleic acids can also be introduced into the chloroplast for expression therein. Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The IMI nucleic acids to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference. If necessary for chloroplast expression, the expression cassette can further comprise a chloroplast promoter operably linked to the IMI nucleic acid. Such chloroplast promoters are known in the art.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, an IMI polynucleotide can be expressed in bacterial cells such as *C. glutamicum*, insect cells, fungal cells, or mammalian cells (such as Chinese hamster ovary cells (CHO) or COS cells), algae, ciliates, plant cells, fungi, or other microorganisms like *C. glutamicum*. Other suitable host cells are known to those skilled in the art.

A host cell of the invention, such as a prokaryotic or eukaryotic host cell in culture, can be used to produce (i.e., express) an IMI polynucleotide. Accordingly, the invention further provides methods for producing IMI polypeptides using the host cells of the invention. In one embodiment, the method comprises culturing the host cell of invention (into which a recombinant expression vector encoding an IMI polypeptide has been introduced, or into which genome has been introduced a gene encoding a wild-type or IMI polypeptide) in a suitable medium until IMI polypeptide is produced. In another embodiment, the method further comprises isolating IMI polypeptides from the medium or the host cell. Another aspect of the invention pertains to isolated IMI polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of IMI polypeptide in which the polypeptide is separated from some of the cellular components of the cells in which it is naturally or recombinantly produced. In one embodiment, the language "substantially free of cellular material" includes preparations of an IMI polypeptide having less than about 30% (by dry weight) of non-IMI material (also referred to herein as a "contaminating polypeptide"), more preferably less than about 20% of non-IMI material, still more preferably less than about 10% of non-IMI material, and most preferably less than about 5% non-IMI material.

When the IMI polypeptide, or biologically active portion thereof, is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of IMI polypeptide in which the polypeptide is separated from chemical precursors or other chemicals that are involved in the synthesis of the polypeptide. In one embodiment, the language "substantially free of chemical precursors or other chemicals" includes preparations of an IMI polypeptide having less than about 30% (by dry weight) of chemical precursors or chemicals, more preferably less than about 20% chemical precursors or chemicals, still more preferably less than about 10% chemical precursors or chemicals, and most preferably less than about 5% chemical precursors or chemicals. In preferred embodiments, isolated polypeptides, or biologically active portions thereof, lack contaminating polypeptides from the same organism from which the IMI polypeptide is derived. Typically, such polypeptides are produced by recombinant expression of, for example, a *Triticum aestivum* IMI polypeptide in plants other than *Triticum aestivum* or microorganisms such as *C. glutamicum*, ciliates, algae, or fungi.

The IMI polynucleotide and polypeptide sequences of the invention have a variety of uses. The nucleic acid and amino acid sequences of the present invention can be used to transform plants, thereby modulating the plant's tolerance to imidazolinone herbicides. Accordingly, the invention provides a method of producing a transgenic plant having increased tolerance to an imidazolinone herbicide comprising, (a) transforming a plant cell with one or more expression vectors comprising one or more IMI nucleic acids, and (b) generating from the plant cell a transgenic plant with an increased tolerance to an imidazolinone herbicide as compared to a wild type plant. In one embodiment, the multiple IMI nucleic acids are derived from different genomes. Also included in the present invention are methods of producing a transgenic plant having increased tolerance to an imidazolinone herbicide comprising, (a) transforming a plant cell with an expression vector comprising an IMI nucleic acid, wherein the nucleic acid is a non-Imi1 nucleic acid and (b) generating from the plant cell a transgenic plant with an increased tolerance to an imidazolinone herbicide as compared to a wild type plant.

The present invention includes methods of modifying a plant's tolerance to an imidazolinone herbicide comprising modifying the expression of one or more IMI nucleic acids. The plant's tolerance to the imidazolinone herbicide can be increased or decreased as achieved by increasing or decreasing the expression of an IMI polynucleotide, respectively. Preferably, the plant's tolerance to the imidazolinone herbicide is increased by increasing expression of an IMI polynucleotide. Expression of an IMI polynucleotide can be modified by any method known to those of skill in the art. The methods of increasing expression of IMI polynucleotides can be used wherein the plant is either transgenic or not transgenic. In cases when the plant is transgenic, the plant can be transformed with a vector containing any of the above described IMI coding nucleic acids, or the plant can be transformed with a promoter that directs expression of endogenous IMI polynucleotides in the plant, for example. The invention provides that such a promoter can be tissue specific or developmentally regulated. Alternatively, non-transgenic plants can have endogenous IMI polynucleotide expression modified by inducing a native promoter. The expression of polynucleotides comprising a polynucleotide sequence as defined in SEQ ID NO:1 in target plants can be accomplished by, but is not limited to, one of the following examples: (a) constitutive promoter, (b) chemical-induced promoter, and (c) engineered promoter over-expression with for example zinc-finger derived transcription factors (Greisman and Pabo, 1997, Science 275:657).

In a preferred embodiment, transcription of the IMI polynucleotide is modulated using zinc-finger derived transcription factors (ZFPs) as described in Greisman and Pabo, 1997, Science 275:657 and manufactured by Sangamo Biosciences, Inc. These ZFPs comprise both a DNA recognition domain and a functional domain that causes activation or repression of a target nucleic acid such as an IMI nucleic acid. Therefore, activating and repressing ZFPs can be created that specifically recognize the IMI polynucleotide promoters described above and used to increase or decrease IMI polynucleotide expression in a plant, thereby modulating the herbicide tolerance of the plant.

As described in more detail above, the plants produced by the methods of the present invention can be monocots or dicots. The plants can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and forage crops, for example. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover. In a preferred embodiment, the plant is a wheat plant or triticale plant. In each of the methods described above, the plant cell includes, but is not limited to, a protoplast, gamete producing cell, and a cell that regenerates into a whole plant. As used herein, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extrachromosomal element, so that it is passed on to successive generations.

As described above, the present invention teaches compositions and methods for increasing the imidazolinone tolerance of a plants or seed as compared to a wild-type plant or seed. In a preferred embodiment, the imidazolinone tolerance of a wheat plant or seed is increased such that the plant or seed can withstand an imidazolinone herbicide application of preferably approximately 10-300 g ai ha$^{-1}$, more preferably 20-160 g ai ha$^{-1}$, and most preferably 40-80 g ai ha$^{-1}$. As used herein, to "withstand" an imidazolinone herbicide application means that the plant is either not killed or not injured by such application.

The present invention provides plants, plant parts, plant organs, plant tissues, plant cells, seed, and host cells with increased tolerance to at least one imidazolinone herbicide when compared to a wild-type, plant, plant part, plant organ, plant tissue, plant cell, seed, or host cell, respectively. By such a "wild-type plant, plant part, plant organ, plant tissue, plant cell, seed, or host cell" is intended that the plant, plant part, plant organ, plant tissue, plant cell, seed, or host cell, respectively, is wild-type with respect to the herbicide-tolerance characteristics of the plant of ATCC Patent Deposit Number 5625 and/or the IMI nucleic acids of the present invention. That is, such a wild-type plant, plant part, plant organ, plant tissue, plant cell, seed, or host cell does not comprise the herbicide-resistance characteristics of the plant of ATCC Patent Deposit Number 5625 and/or does not comprise the IMI nucleic acids of the present invention. The use of the term "wild-type" is not, therefore, intended to imply that a plant, plant part, plant organ, plant tissue, plant cell, seed, or host cell lacks recombinant DNA in its genome, and/or does not comprise herbicide tolerance characteristics and/or IMI nucleic acids that are different from those herbicide tolerance characteristics and IMI nucleic acids of the present invention.

Additionally provided herein is a method of controlling weeds within the vicinity of a wheat or triticale plant, comprising applying an imidazolinone herbicide to the weeds and to the wheat or triticale plant, wherein the wheat or triticale plant has increased tolerance to the imidazolinone herbicide as compared to a wild type wheat or triticale plant, and wherein the imidazolinone tolerant wheat or triticale plant comprises at least one IMI nucleic acid. In one embodiment, the plant comprises multiple IMI nucleic acids. In another embodiment, the plant comprises an Imi1 nucleic acid. By providing for wheat and triticale plants having increased tolerance to imidazolinone, a wide variety of formulations can be employed for protecting wheat and triticale plants from weeds, so as to enhance plant growth and reduce competition for nutrients. An imidazolinone herbicide can be used by itself for pre-emergence, post-emergence, pre-planting, and at-planting control of weeds in areas surrounding the wheat plants described herein or an imidazolinone herbicide formulation can be used that contains other additives. The imidazolinone herbicide can also be used as a seed treatment. Additives found in an imidazolinone herbicide formulation include other herbicides, detergents, adjuvants, spreading agents, sticking agents, stabilizing agents, or the like. The imidazolinone herbicide formulation can be a wet or dry preparation and can include, but is not limited to, flowable powders, emulsifiable concentrates, and liquid concentrates. The imidazolinone herbicide and herbicide formulations can be applied in accordance with conventional methods, for example, by spraying, irrigation, dusting, or the like.

The present invention further provides transformation vectors comprising a selectable marker gene of the invention. The selectable marker gene comprises a promoter that drives expression in a host cell operably linked to a IMI nucleic acid of the invention. The transformation vector can additionally comprise a gene of interest to be expressed in the host cell and can also, if desired, include a chloroplast-targeting sequence that is operably linked to the polynucleotide of the invention.

The present invention further provides methods for using the transformation vectors of the invention to select for cells transformed with the gene of interest. Such methods involve the transformation of a host cell with the transformation vector, exposing the cell to a level of an imidazolinone or sulfonylurea herbicide that would kill or inhibit the growth of a non-transformed host cell, and identifying the transformed host cell by its ability to grow in the presence of the herbicide. In one embodiment of the invention, the host cell is a plant cell and the selectable marker gene comprises a promoter that drives expression in a plant cell.

The transformation vectors of the invention can be used to produce plants transformed with a gene of interest. The transformation vector will comprise a selectable marker gene of the invention and a gene of interest to be introduced and typically expressed in the transformed plant. Such a selectable marker gene comprises an IMI nucleic acid of the invention operably linked to a promoter that drives expression in a host cell. The IMI nucleic acid comprises the polynucleotide sequence set forth in SEQ ID NO:1, a polynucleotide sequence encoding the amino acid sequence set forth in SEQ ID NO:2, and functional fragments and variants of either of these polynucleotide sequences, wherein the fragment or variant encodes a polypeptide that comprises an alanine to threonine substitution at position 96 corresponding to a wild type AHAS polypeptide. For use in plants and plant cells, the transformation vector comprises a selectable marker gene comprising an IMI nucleic acid of the invention operably linked to a promoter that drives expression in a plant cell.

The invention also relates to a plant expression vector comprising a promoter that drives expression in a plant operably linked to an IMI nucleic acid of the invention. The IMI nucleic acid comprises the polynucleotide sequence set forth in SEQ ID NO:1, a polynucleotide sequence encoding the amino acid sequence set forth in SEQ ID NO:2, and functional fragments and variants of either of these polynucleotide sequences, wherein the fragment or variant encodes a polypeptide that comprises an alanine to threonine substitution at position 96 corresponding to a wild type AHAS polypeptide. The plant expression vector of the invention does not depend on a particular promoter, only that such a promoter is capable of driving gene expression in a plant cell. Preferred promoters include constitutive promoters and tissue-preferred promoters.

The genes of interest of the invention vary depending on the desired outcome. For example, various changes in phenotype can be of interest including modifying the fatty acid composition in a plant, altering the amino acid content of a plant, altering a plant's insect and/or pathogen defense mechanisms, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

In one embodiment of the invention, the genes of interest include insect resistance genes such as, for example, *Bacillus thuringiensis* toxin protein genes (U.S. Pat. Nos. 5,366,892; 5,747,450; 5,736,514; 5,723,756; 5,593,881; and Geiser et al. (1986) *Gene* 48:109).

The IMI proteins or polypeptides of the invention can be purified from, for example, canola plants and can be used in compositions. Also, an isolated IMI nucleic acid encoding an IMI protein of the invention can be used to express an IMI protein of the invention in a microbe such as *E. coli* or a yeast. The expressed IMI protein can be purified from extracts of *E. coli* or yeast by any method known to those or ordinary skill in the art.

In certain embodiments of the invention, the methods involve the use of herbicide-tolerant or herbicide-resistant plants. By an "herbicide-tolerant" or "herbicide-resistant" plant, it is intended that a plant that is tolerant or resistant to at least one herbicide at a level that would normally kill, or inhibit the growth of, a normal or wild-type plant. In one embodiment of the invention, the herbicide-tolerant plants of the invention comprise an IMI nucleic acid that encodes an IMI protein.

For the present invention, the terms "herbicide-tolerant" and "herbicide-resistant" are used interchangeable and are intended to have an equivalent meaning and an equivalent scope. Similarly, the terms "herbicide-tolerance" and "herbicide-resistance" are used interchangeable and are intended to have an equivalent meaning and an equivalent scope. Likewise, the terms "imidazolinone-resistant" and "imidazolinone-resistance" are used interchangeable and are intended to be of an equivalent meaning and an equivalent scope as the terms "imidazolinone-tolerant" and "imidazolinone-tolerance", respectively.

The present invention provides plants, plant tissues, plant cells, and host cells with increased resistance or tolerance to at least one herbicide, particularly a herbicide that interferes with the activity of the AHAS enzyme, more particularly an imidazolinone or sulfonylurea herbicide. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, microspore, or host cell, but that said amount does not kill or inhibit as severely the growth of the herbicide-resistant plants, plant tissues, plant cells, microspores, and host cells of the present invention. Typically, the effective amount of a herbicide is an amount that is routinely used in agricultural production systems to kill weeds of interest. Such an amount is known to those of ordinary skill in the art, or can be easily determined using methods known in the art. Furthermore, it is recognized that the effective amount of a herbicide in an agricultural production system might be substantially different than an effective amount of a herbicide in an in vitro plant culture system.

The IMI nucleic acids of the present invention may be used for transformation of any plant species, including, but not limited to, monocots and dicots. Examples of plant species of interest include, but are not limited to, corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum, T. Turgidum* ssp. *durum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. Preferably, plants of the present invention are crop plants (for example, sunflower, *Brassica* sp., cotton, sugar, beet, soybean, peanut, alfalfa, safflower, tobacco, corn, rice, wheat, rye, barley triticale, sorghum, millet, etc.).

The herbicide resistant plants of the invention find use in methods for controlling weeds. Thus, the present invention further provides a method for controlling weeds in the vicinity of a herbicide-resistant plant of the invention. The method comprises applying an effective amount of a herbicide to the weeds and to the herbicide-resistant plant, wherein the plant has increased resistance to at least one herbicide, particularly an imidazolinone or sulfonylurea herbicide, when compared to a wild-type plant. In such a method for controlling weeds, the herbicide-resistant plants of the invention are preferably crop plants, including, but not limited to, sunflower, alfalfa, *Brassica* sp., soybean, cotton, safflower, peanut, tobacco, tomato, potato, wheat, rice, maize, sorghum, barley, rye, millet, and sorghum.

By providing plants having increased resistance to herbicides, particularly imidazolinone and sulfonylurea herbicides, a wide variety of formulations can be employed for protecting plants from weeds, so as to enhance plant growth and reduce competition for nutrients. A herbicide can be used by itself for pre-emergence, post-emergence, pre-planting and at planting control of weeds in areas surrounding the plants described herein or an imidazolinone herbicide formulation can be used that contains other additives. The herbicide can also be used as a seed treatment. That is an effective concentration or an effective amount of the herbicide, or a composition comprising an effective concentration or an effective amount of the herbicide can be applied directly to the seeds prior to or during the sowing of the seeds. Additives found in an imidazolinone or sulfonylurea herbicide formulation or composition include other herbicides, detergents, adjuvants, spreading agents, sticking agents, stabilizing agents, or the like. The herbicide formulation can be a wet or dry preparation and can include, but is not limited to, flowable powders, emulsifiable concentrates and liquid concentrates. The herbicide and herbicide formulations can be applied in accordance with conventional methods, for example, by spraying, irrigation, dusting, coating, and the like.

The present invention provides non-transgenic and transgenic seeds with increased tolerance to at least one herbicide, particularly an AHAS-inhibiting herbicide, more particularly an imidazolinone herbicide. Such seeds include, for example, non-transgenic wheat seeds comprising the herbicide-tolerance characteristics of the plant with ATCC Patent Deposit Number 5625, and transgenic seeds comprising an IMI nucleic acid molecule of the invention that encodes a IMI protein.

The present invention provides methods for producing a herbicide-resistant plant, particularly a herbicide-resistant wheat or triticale plant, through conventional plant breeding involving sexual reproduction. The methods comprise crossing a first plant that is resistant to a herbicide to a second plant that is not resistant to the herbicide. The first plant can be any of the herbicide resistant plants of the present invention including, for example, transgenic plants comprising at least one of the polynucleotides of the present invention that encode a herbicide resistant IMI protein and non-transgenic wheat plants that comprise the herbicide-tolerance characteristics of the wheat plant with ATCC Patent Deposit Number 5625. The second plant can be any plant that is capable of producing viable progeny plants (i.e., seeds) when crossed with the first plant. Typically, but not necessarily, the first and second plants are of the same species. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The methods of the invention can additionally involve selecting plants that comprise the herbicide tolerance characteristics of the first plant.

The present invention further provides methods for increasing the herbicide-resistance of a plant, particularly a herbicide-resistant wheat plant, through conventional plant breeding involving sexual reproduction. The methods comprise crossing a first plant that is resistant to a herbicide to a second plant that may or may not be resistant to the herbicide or may be resistant to different herbicide or herbicides than the first plant. The first plant can be any of the herbicide resistant plants of the present invention including, for example, transgenic plants comprising at least one of the IMI nucleic acids of the present invention that encode IMI protein and non-transgenic wheat and triticale plants that comprise the herbicide-tolerance characteristics of the wheat plant with ATCC Patent Deposit Number 5625. The second plant can be any plant that is capable of producing viable progeny plants (i.e., seeds) when crossed with the first plant. Typically, but not necessarily, the first and second plants are of the same species. The progeny plants produced by this method of the present invention have increased resistance to a herbicide when compared to either the first or second plant or both. When the first and second plants are resistant to different herbicides, the progeny plants will have the combined herbicide tolerance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The methods of the invention can additionally involve selecting plants that comprise the herbicide tolerance characteristics of the first plant, the second plant, or both the first and the second plant.

The plants of the present invention can be transgenic or non-transgenic. An example of a non-transgenic wheat plant having increased resistance to imidazolinone is the wheat plant (Shiloh-8) having ATCC Patent Deposit No. 5625; or mutant, recombinant, or a genetically engineered derivative of the plant having ATCC Patent Deposit No. 5625; or of any progeny of the plant having ATCC Patent Deposit No. 5625; or a plant that is a progeny of any of these plants; or a plant that comprises the herbicide tolerance characteristics of the plant having ATCC Patent Deposit No. 5625.

The present invention also provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

The present invention provides methods that involve the use of at least one AHAS-inhibiting herbicide selected from the group consisting of imidazolinone herbicides, sulfonylurea herbicides, triazolopyrimidine herbicides, pyrimidinyloxybenzoate herbicides, sulfonylamino-carbonyltriazolinone herbicides, and mixtures thereof. In these methods, the AHAS-inhibiting herbicide can be applied by any method known in the art including, but not limited to, seed treatment, soil treatment, and foliar treatment.

Prior to application, the AHAS-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

Examples of suitable carriers are ground natural minerals (for example kaolins, clays, talc, chalk) and ground synthetic minerals (for example highly disperse silica, silicates).

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example Dichlorophen und enzylalkoholhemiformal.

Seed Treatment formulations may additionally comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An examples of a suitable gelling agent is carrageen (Satiagel®).

Powders, materials for spreading, and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the AHAS-inhibiting herbicide. In this case, the AHAS-inhibiting herbicides are employed in a purity of from 90% to 100% by weight, preferably 95% to 100% by weight (according to NMR spectrum). For seed treatment purposes, respective formulations can be diluted 2-10 fold leading to concentrations in the ready to use preparations of 0.01 to 60% by weight active compound by weight, preferably 0.1 to 40% by weight.

The AHAS-inhibiting herbicide can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the AHAS-inhibiting herbicide according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The AHAS-inhibiting herbicide may also be used successfully in the ultra-low-volume process (ULV), it being possible to apply formulations comprising over 95% by weight of active compound, or even to apply the active compound without additives.

The following are examples of formulations:
1. Products for dilution with water for foliar applications. For seed treatment purposes, such products may be applied to the seed diluted or undiluted.
   A) Water-soluble concentrates (SL, LS)
   Ten parts by weight of the AHAS-inhibiting herbicide are dissolved in 90 parts by weight of water or a water-soluble solvent. As an alternative, wetters or other auxiliaries are added. The AHAS-inhibiting herbicide dissolves upon dilution with water, whereby a formulation with 10% (w/w) of AHAS-inhibiting herbicide is obtained.
   B) Dispersible concentrates (DC)
   Twenty parts by weight of the AHAS-inhibiting herbicide are dissolved in 70 parts by weight of cyclohexanone with addition of 10 parts by weight of a dispersant, for example polyvinylpyrrolidone. Dilution with water gives a dispersion, whereby a formulation with 20% (w/w) of AHAS-inhibiting herbicide is obtained.
   C) Emulsifiable concentrates (EC)
   Fifteen parts by weight of the AHAS-inhibiting herbicide are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of AHAS-inhibiting herbicide is obtained.
   D) Emulsions (EW, EO, ES)
   Twenty-five parts by weight of the AHAS-inhibiting herbicide are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of AHAS-inhibiting herbicide is obtained.
   E) Suspensions (SC, OD, FS)
   In an agitated ball mill, 20 parts by weight of the AHAS-inhibiting herbicide are comminuted with addition of 10 parts by weight of dispersants, wetters and 70 parts by weight of water or of an organic solvent to give a fine AHAS-inhibiting herbicide suspension. Dilution with water gives a stable suspension of the AHAS-inhibiting herbicide, whereby a formulation with 20% (w/w) of AHAS-inhibiting herbicide is obtained.

F) Water-dispersible granules and water-soluble granules (WG, SG)

Fifty parts by weight of the AHAS-inhibiting herbicide are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the AHAS-inhibiting herbicide, whereby a formulation with 50% (w/w) of AHAS-inhibiting herbicide is obtained.

G) Water-dispersible powders and water-soluble powders (WP, SP, SS, WS)

Seventy-five parts by weight of the AHAS-inhibiting herbicide are ground in a rotor-stator mill with addition of 25 parts by weight of dispersants, wetters and silica gel. Dilution with water gives a stable dispersion or solution of the AHAS-inhibiting herbicide, whereby a formulation with 75% (w/w) of AHAS-inhibiting herbicide is obtained.

I) Gel-Formulation (GF)

In an agitated ball mill, 20 parts by weight of the AHAS-inhibiting herbicide are comminuted with addition of 10 parts by weight of dispersants, 1 part by weight of a gelling agent wetters and 70 parts by weight of water or of an organic solvent to give a fine AHAS-inhibiting herbicide suspension. Dilution with water gives a stable suspension of the AHAS-inhibiting herbicide, whereby a formulation with 20% (w/w) of AHAS-inhibiting herbicide is obtained. This gel formulation is suitable for us as a seed treatment.

2. Products to be applied undiluted for foliar applications. For seed treatment purposes, such products may be applied to the seed diluted.

A) Dustable powders (DP, DS)

Five parts by weight of the AHAS-inhibiting herbicide are ground finely and mixed intimately with 95 parts by weight of finely divided kaolin. This gives a dustable product having 5% (w/w) of AHAS-inhibiting herbicide.

B) Granules (GR, FG, GG, MG)

One-half part by weight of the AHAS-inhibiting herbicide is ground finely and associated with 95.5 parts by weight of carriers, whereby a formulation with 0.5% (w/w) of AHAS-inhibiting herbicide is obtained. Current methods are extrusion, spray-drying or the fluidized bed. This gives granules to be applied undiluted for foliar use.

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

The present invention non-transgenic and transgenic seeds of the herbicide-resistant plants of the present invention. Such seeds include, for example, non-transgenic wheat seeds comprising the herbicide-tolerance characteristics of the plant with ATCC Patent Deposit Number 5625, and transgenic seeds comprising a polynucleotide molecule of the invention that encodes an IMI protein.

For seed treatment, seeds of the herbicide resistant plants according of the present invention are treated with herbicides, preferably herbicides selected from the group consisting of AHAS-inhibiting herbicides such as amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, and mixtures thereof, or with a formulation comprising a AHAS-inhibiting herbicide.

The term seed treatment comprises all suitable seed treatment techniques known in the art, such as seed dressing, seed coating, seed dusting, seed soaking, and seed pelleting.

In accordance with one variant of the present invention, a further subject of the invention is a method of treating soil by the application, in particular into the seed drill: either of a granular formulation containing the AHAS-inhibiting herbicide as a composition/formulation (e.g. a granular formulation, with optionally one or more solid or liquid, agriculturally acceptable carriers and/or optionally with one or more agriculturally acceptable surfactants. This method is advantageously employed, for example, in seedbeds of cereals, maize, cotton, and sunflower.

The present invention also comprises seeds coated with or containing with a seed treatment formulation comprising at least one AHAS-inhibiting herbicide selected from the group consisting of amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

The seed treatment application with the AHAS-inhibiting herbicide or with a formulation comprising the AHAS-inhibiting herbicide is carried out by spraying or dusting the seeds before sowing of the plants and before emergence of the plants.

In the treatment of seeds, the corresponding formulations are applied by treating the seeds with an effective amount of the AHAS-inhibiting herbicide or a formulation comprising the AHAS-inhibiting herbicide. Herein, the application rates are generally from 0.1 g to 10 kg of the a.i. (or of the mixture of a.i. or of the formulation) per 100 kg of seed, preferably from 1 g to 5 kg per 100 kg of seed, in particular from 1 g to 2.5 kg per 100 kg of seed. For specific crops such as lettuce the rate can be higher.

The present invention provides a method for combating undesired vegetation or controlling weeds comprising contacting the seeds of the resistant plants according to the present invention before sowing and/or after pregermination with an AHAS-inhibiting herbicide. The method can further comprise sowing the seeds, for example, in soil in a field or in a potting medium in greenhouse. The method finds particular use in combating undesired vegetation or controlling weeds in the immediate vicinity of the seed.

The control of undesired vegetation is understood as meaning the killing of weeds and/or otherwise retarding or inhibiting the normal growth of the weeds. Weeds, in the broadest sense, are understood as meaning all those plants which grow in locations where they are undesired.

The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea, Trifolium, Ranunculus,* and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera*.

In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The following examples are offered by way of illustration and not by way of limitation.

EXAMPLE 1

Mutagenesis and Selection of Tolerant Wheat Lines

Samples of 1,500 Shiloh variety seeds were each placed in a 1,000 ml beaker and covered with deionized water to at least 1 inch above the seed level. The beakers were then placed in a refrigerator at 4° C. for 15-20 hours. The seed samples were removed from the refrigerator and brought up to room temperature over an approximately 3 hour period by placing the beaker at room temperature. In some cases, the warming process was accelerated by adding deionized water to the beakers.

The deionized water was drained off the seeds, and the beaker was filled with a sodium azide solution to at least 1 inch above the seed level. The sodium azide solution was prepared by adding 27.218 g $KH_2PO_4$ to 1,500 ml deionized water, bringing the solution to pH 3 with concentrated $H_3PO_4$, and bringing the final solution to 2 L volume with deionized water. Just prior to use, 0.2604 g $NaN_3$ was added, and the solution was kept in the dark. After addition of the sodium azide solution to the seeds, the beakers were incubated in a dark area at room temperature for 2 hours, with occasional stirring.

The sodium azide treatment solution was decanted, and the seed samples were rinsed twice with deionized water. Then the seed samples were covered with deionized water to at least 1 inch above seed level and soaked at room temperature for 1 hour, with occasional stirring. The deionized water was decanted, and the seeds were spread evenly on paper towels to dry. The seeds were planted in the field near Berthoud, Colo. in six 5 feet by 40 feet plots. Approximately 15 pounds of M2 seed were harvested, and approximately 466,000 seeds were planted near Platteville, Colo. The fields were sprayed with 1× (40 g ai ha$^{-1}$ (imazamox)) or 2× (80 g ai ha$^{-1}$ (imazamox)).

Plants tolerant to the herbicide were identified and transplanted into 1 gallon pots, and put into vernalization for 4 weeks at 45° F. Fourteen single plant selections were made out of the 2× rate area. The tolerant M2 plants were taken out of vernalization, grown out in a Berthoud, Colo. greenhouse, and M3 plants were planted in approximately 4 feet by 5 feet plots near Berthoud, Colo. The plots were sprayed with 80 g ai ha$^{-1}$ (imazamox) when the plants were at the three-leaf stage, and the results of the fourteen progenies were rated as shown in Table 1.

TABLE 1

Tolerance of M3 Shiloh plants to 80 g ai ha$^{-1}$ (imazamox)

| All Good MR-R | Medium MR-MS | Discard-Sensitive |
|---|---|---|
| Shiloh-08 | Shiloh-01 | Shiloh-03 |
|  | Shiloh-14 | Shiloh-04 |
|  |  | Shiloh-05 |
|  |  | Shiloh-06 |
|  |  | Shiloh-07 |
|  |  | Shiloh-09 |
|  |  | Shiloh-10 |
|  |  | Shiloh-11 |
|  |  | Shiloh-12 |
|  |  | Shiloh-13 |

Twelve seeds of Shiloh-08 were planted in the Berthoud, Colo. greenhouse and screened with 40 g ai ha$^{-1}$ imazamox at the three-leaf stage, and the results confirmed a heritable homozygous reaction.

Two test-cross experiments of Shiloh-8 with a known Als1 line were performed. Both experiments showed no genetic segregation for tolerance in the F2 populations, suggesting that Shiloh-8 was allelic to Als1 with respect to herbicide tolerance. The results are shown in Tables 2 and 3.

TABLE 2

| Test Cross | Date crossed | Date F2's Harvested | #F2's Screened | F2 Room | FS4? |
|---|---|---|---|---|---|
| iShiloh-8/ iGDN | winter 99-00 | Summer 00 | 168 | 15-40 g | YES all R |

TABLE 3

| EXP 2001-2 Winter Test Cross | Total #F2's | Strong Survivors | Winkled or stunted | Dead or Dying growth point | DGP+ Brown sheath |
|---|---|---|---|---|---|
| iShiloh-8/ imi GDN | 167 | 140 | 27 | 0 | 0 |
| iShiloh-8 | 8 | 7 | 1 | 0 | 0 |
| Shiloh | 7 | 0 | 0 | 0 | 7 |
| imi GDN | 2 | 1 | 1 | 0 | 0 |

EXAMPLE 2

Molecular Characterization of the Shiloh-8 Wheat Line

Subsequent molecular characterization revealed the Shiloh-08 line to harbor a novel adenine to guanine base pair substitution at position 142 of the Als1 gene. This mutant Als1 polynucleotide encodes a mutant AHAS polypeptide that has an alanine to threonine substitution at position 96 corresponding to a wild type AHAS polypeptide and that confers upon the plant tolerance to imidazolinone herbicides. The Shiloh-8 line did not harbor a mutation in the Als2 or Als3 genes.

EXAMPLE 3

Characterization of the Imidazolinone Tolerant Trait of the Shiloh-8 Line

Agronomic and comparative imidazolinone herbicide imazamox tolerance were then evaluated under field conditions. Table 4 summarizes the yield and agronomic evaluations comparing Shiloh-8 and wild type Shiloh plants. These trials were typical cereal evaluation experiments using incomplete randomized block three replication design. Plots were 1.54 m×4.62 m at harvest. Table 5 summarizes multiple field imidazolinone herbicide imazamox tolerance comparisons between Shiloh-8 and the standard tolerant control 9804. These plots ranged from a single row 1 m to larger 1.54 m×4.62 m plots.

TABLE 4

| PLANT | 5 Loc yield | (lbs/bu) Test Weigt | Facultative (1-9) | Heading | Apr. 12, 2001 ZADOKS | Height | SOIL VIRUS | *Septoria tritici* | Bacterial streak | Tan spot | Stripe Rust |
|---|---|---|---|---|---|---|---|---|---|---|---|
| Shiloh | 67.6 | 58.9 | 6 | 108 | 52 | 36.3 | 1 | 5 | 6 | 4 | 3 |
| Shiloh-8 | 61.5 | 59.1 | 6 | 109 | 52 | 34.8 | 1 | 4 | 5 | 5 | 1 |
| AVERGE | 64.5 | 59.0 | 6 | 108 | 52 | 35.6 | 1 | 5 | 6 | 4 | 2 |
| CV | 6.8 | | 1 = Facultative | | | | | | | | |
| LSD (.10) | 7.4 | | 9 = Non-venaized | | | | | | | | |
| 30 entry trial | | | | | | | | | | | |

TABLE 5

| 9804/ Mutant | Fall '98 M2 Plant Rating (8 oz/ac)[1] | Spr '99 M3 Progeny Rating (8 oz/ac) Gmhse | Sum '99 M3 Progeny Rating (8 oz/ac) Field | '99-'00 Rate D&O | | | | | |
|---|---|---|---|---|---|---|---|---|---|
| | | | | Plateville, CO | | Quinter, KS[2] | | | |
| | | | | (early) | | (early) | | (late) | |
| | | | | 4 oz/ac | 8 oz/ac | 4 oz/ac | 8 oz/ac | 4 oz/ac | 8 oz/ac |
| 9604 (iFEDEL) | R | R | R | 1 | 2 | 1 | 2 | 8 | 8 |
| iSHILOH-08 | R | R | R-MR | 2 | 3 | 2 | 3 | 5 | 6 |
| | | | | 1-no effect 10-dead | | | | | |

[1] Field applied, transplant for greenhouse finish and rating
[2] Spring application, temperature dropped 19° F. the night following application All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A wheat or triticale plant, wherein the plant is obtained by a process comprising crossing a plant of line Shiloh-8, a representative sample of seed of the line having been deposited with American Type Culture Collection (ATCC) under Patent Deposit Designation Number PTA-5625, with another wheat or triticale variety, wherein the plant comprises a Shiloh-8 Imi1 nucleic acid, said Shiloh-8 Imi1 nucleic acid comprising a polynucleotide sequence encoding an IMI polypeptide having an alanine to threonine substitution in Domain C, said polynucleotide sequence is that of the D genome, and said plant having increased tolerance to the imidazolinone herbicide as compared to that of a wild-type wheat or triticale plant.

2. The plant of claim 1, wherein the imidazolinone herbicide comprises at least one of: imazethapyr, imazapic, imazamox, imazaquin, imazetabenz, imazapyr, a mixture of imazapyr and imazamox, or a combination thereof.

3. The plant of claim 1, wherein the imidazolinone herbicide comprises imazethapyr.

4. The plant of claim 1, wherein the imidazolinone herbicide comprises imazamox.

5. The plant of claim 1, wherein the Shiloh-8 Imi nucleic acid comprises an Imi1 nucleic acid.

6. The plant of claim 1, wherein the Shiloh-8 Imi nucleic acid comprises the polynucleotide sequence set forth in SEQ ID NO:1.

7. The plant of claim 1, wherein the Shiloh-8 Imi nucleic acid encodes an IMI polypeptide comprising the amino acid sequence set forth in SEQ ID NO:2.

8. The plant of claim 1, wherein the plant is non-transgenic.

9. The plant of claim 1, wherein the plant is transgenic.

10. The plant of claim 1, wherein the plant comprises a non-mutated AHAS gene at its Als2 or Als3 loci.

11. The seed of the plant of claim 1, said seed comprises a Shiloh-8 Imi1 nucleic acid, said Shiloh-8 Imi1 nucleic acid comprising a polynucleotide sequence encoding an IMI polypeptide having an alanine to threonine substitution in Domain C, said polynucleotide sequence is that of the D genome, and a plant grown from said seed exhibits increased tolerance to an imidazolinone herbicide as compared to that of a wild-type wheat or triticale plant.

12. The seed of claim 11, wherein said seed further comprises a seed treatment.

13. The seed of claim 12, wherein said seed treatment comprises an herbicidal composition.

14. The seed of claim 13, wherein said herbicidal composition comprises an imidazolinone herbicide.

15. The seed of claim 14, wherein said imidazolinone herbicide comprises at least one of: imazethapyr, imazapic, imazamox, imazaquin, imazetabenz, imazapyr, a mixture of imazapyr and imazamox, or a combination thereof.

16. The seed of claim 14, wherein the imidazolinone herbicide comprises imazethapyr.

17. The seed of claim 14, wherein the imidazolinone herbicide comprises imazamox.

* * * * *

SEQUENCE LISTING

```
<160> NUMBER OF SEQ ID NOS: 6

<210> SEQ ID NO 1
<211> LENGTH: 1788
<212> TYPE: DNA
<213> ORGANISM: Triticum aestivum
<220> FEATURE:
<221> NAME/KEY: CDS
<222> LOCATION: (1)...(1788)

<400> SEQUENCE: 1 tcc ccc gcc gcc acc tcc gcc gcg cct ccc gca acc gcg ctc cgg ccc      48
Ser Pro Ala Ala Thr Ser Ala Ala Pro Pro Ala Thr Ala Leu Arg Pro
1               5                   10                  15 tgg ggc ccg tcc gag ccc cgc aag ggc gcc gac atc ctc gtc gag gcg      96
Trp Gly Pro Ser Glu Pro Arg Lys Gly Ala Asp Ile Leu Val Glu Ala
                20                  25                  30 ctc gag cgc tgc ggc atc gtc gac gtc ttc gcc tac ccc ggc ggc acc     144
Leu Glu Arg Cys Gly Ile Val Asp Val Phe Ala Tyr Pro Gly Gly Thr
            35                  40                  45 tcc atg gag atc cac cag gcg ctg acg cgc tcg ccc gtc atc acc aac     192
Ser Met Glu Ile His Gln Ala Leu Thr Arg Ser Pro Val Ile Thr Asn
        50                  55                  60 cac ctc ttc cgc cac gag cag ggg gag gcg ttc gcg gcg tcc ggc tac     240
His Leu Phe Arg His Glu Gln Gly Glu Ala Phe Ala Ala Ser Gly Tyr
65                  70                  75                  80 gcc cgc gcg tcc ggc cgc gtc ggc gtc tgc gtc gcc acc tcc ggc ccg     288
Ala Arg Ala Ser Gly Arg Val Gly Val Cys Val Ala Thr Ser Gly Pro
                85                  90                  95 ggg gcc acc aac ctc gtc tcc gcg ctc gcc gac gcc ctc ctc gac tcc     336
Gly Ala Thr Asn Leu Val Ser Ala Leu Ala Asp Ala Leu Leu Asp Ser
                100                 105                 110 atc ccc atg gtc gcc atc acg ggc cag gtc ccc cgc cgc atg atc ggc     384
Ile Pro Met Val Ala Ile Thr Gly Gln Val Pro Arg Arg Met Ile Gly
            115                 120                 125 acg gac gcg ttc cag gag acg ccc ata gtg gag gtc acg cgc tcc atc     432
Thr Asp Ala Phe Gln Glu Thr Pro Ile Val Glu Val Thr Arg Ser Ile
        130                 135                 140 acc aag cac aac tac ctg gtc ctt gac gtg gag gat atc ccc cgc gtc     480
Thr Lys His Asn Tyr Leu Val Leu Asp Val Glu Asp Ile Pro Arg Val
145                 150                 155                 160 atc cag gaa gcc ttc ttc ctt gca tcc tct ggc cgc ccg ggg ccg gtg     528
Ile Gln Glu Ala Phe Phe Leu Ala Ser Ser Gly Arg Pro Gly Pro Val
                165                 170                 175 cta gtt gat atc ccc aag gac atc cag cag cag atg gct gtg ccc gtc     576
Leu Val Asp Ile Pro Lys Asp Ile Gln Gln Gln Met Ala Val Pro Val
            180                 185                 190 tgg gac act cca atg agt ttg cca ggg tac atc gcc cgc ctg ccc aag     624
Trp Asp Thr Pro Met Ser Leu Pro Gly Tyr Ile Ala Arg Leu Pro Lys
        195                 200                 205 cca cca tct act gaa tcg ctt gag cag gtc ctg cgt ctg gtt ggc gag     672
Pro Pro Ser Thr Glu Ser Leu Glu Gln Val Leu Arg Leu Val Gly Glu
            210                 215                 220
```

```
                                              -continued tca cgg cgc cca att ctg tat gtt ggt ggt ggc tgc gct gcg tct ggc      720
Ser Arg Arg Pro Ile Leu Tyr Val Gly Gly Gly Cys Ala Ala Ser Gly
225                 230                 235                 240 gag gag ttg cgc cgc ttt gtt gag ctt act ggg att cca gtt aca act      768
Glu Glu Leu Arg Arg Phe Val Glu Leu Thr Gly Ile Pro Val Thr Thr
            245                 250                 255 act ctg atg ggc ctt ggc aac ttc ccc agc gac gac cca ctg tct ctg      816
Thr Leu Met Gly Leu Gly Asn Phe Pro Ser Asp Asp Pro Leu Ser Leu
        260                 265                 270 cgc atg ctt ggg atg cat ggc act gtg tat gca aat tat gca gta gat      864
Arg Met Leu Gly Met His Gly Thr Val Tyr Ala Asn Tyr Ala Val Asp
    275                 280                 285 aag gct gac ctg ttg ctc gca ttt ggt gtg cgg ttt gat gat cgt gtg      912
Lys Ala Asp Leu Leu Leu Ala Phe Gly Val Arg Phe Asp Asp Arg Val
290                 295                 300 act ggg aaa atc gag gct ttt gca agc agg tcc aag att gtg cac att      960
Thr Gly Lys Ile Glu Ala Phe Ala Ser Arg Ser Lys Ile Val His Ile
305                 310                 315                 320 gac att gac cca gct gag att ggc aag aac aag cag cca cat gtc tcc     1008
Asp Ile Asp Pro Ala Glu Ile Gly Lys Asn Lys Gln Pro His Val Ser
            325                 330                 335 att tgt gca gat gtt aag ctt gct tta cag ggg ttg aat gat cta tta     1056
Ile Cys Ala Asp Val Lys Leu Ala Leu Gln Gly Leu Asn Asp Leu Leu
        340                 345                 350 aat ggg agc aaa gca caa cag ggt ctg gat ttt ggt cca tgg cac aag     1104
Asn Gly Ser Lys Ala Gln Gln Gly Leu Asp Phe Gly Pro Trp His Lys
    355                 360                 365 gag ttg gat cag cag aag agg gag ttt cct cta gga ttc aag act ttt     1152
Glu Leu Asp Gln Gln Lys Arg Glu Phe Pro Leu Gly Phe Lys Thr Phe
370                 375                 380 ggc gag gcc atc ccg ccg caa tat gct atc cag gta ctg gat gag ctg     1200
Gly Glu Ala Ile Pro Pro Gln Tyr Ala Ile Gln Val Leu Asp Glu Leu
385                 390                 395                 400 aca aaa ggg gag gcg atc att gcc act ggt gtt ggg cag cac cag atg     1248
Thr Lys Gly Glu Ala Ile Ile Ala Thr Gly Val Gly Gln His Gln Met
            405                 410                 415 tgg gcg gct cag tat tac act tac aag cgg cca cgg cag tgg ctg tct     1296
Trp Ala Ala Gln Tyr Tyr Thr Tyr Lys Arg Pro Arg Gln Trp Leu Ser
        420                 425                 430 tcg tct ggt ttg ggg gca atg gga ttt ggg tta cca gct gca gct ggc     1344
Ser Ser Gly Leu Gly Ala Met Gly Phe Gly Leu Pro Ala Ala Ala Gly
    435                 440                 445 gct gct gtg gcc aac cca ggt gtt aca gtt gtt gac att gat ggt gat     1392
Ala Ala Val Ala Asn Pro Gly Val Thr Val Val Asp Ile Asp Gly Asp
450                 455                 460 ggt agt ttc ctc atg aac att cag gag ttg gcg ttg atc cgc att gag     1440
Gly Ser Phe Leu Met Asn Ile Gln Glu Leu Ala Leu Ile Arg Ile Glu
465                 470                 475                 480 aac ctc cca gtg aag gtg atg ata ttg aac aac cag cat ctg gga atg     1488
Asn Leu Pro Val Lys Val Met Ile Leu Asn Asn Gln His Leu Gly Met
            485                 490                 495 gtg gtg cag tgg gag gat agg ttt tac aag gcc aat cgg gcg cac aca     1536
Val Val Gln Trp Glu Asp Arg Phe Tyr Lys Ala Asn Arg Ala His Thr
        500                 505                 510 tac ctt ggc aac cca gaa aat gag agt gag ata tat cca gat ttt gtg     1584
Tyr Leu Gly Asn Pro Glu Asn Glu Ser Glu Ile Tyr Pro Asp Phe Val
    515                 520                 525 acg att gct aaa gga ttc aac gtt cca gca gtt cga gtg acg aag aag     1632
Thr Ile Ala Lys Gly Phe Asn Val Pro Ala Val Arg Val Thr Lys Lys
530                 535                 540
```

```
agc gaa gtc act gca gca atc aag aag atg ctt gag acc cca ggg cca   1680
Ser Glu Val Thr Ala Ala Ile Lys Lys Met Leu Glu Thr Pro Gly Pro
545                 550                 555                 560 tac ttg ttg gat atc ata gtc ccg cat cag gag cac gtg ctg cct atg   1728
Tyr Leu Leu Asp Ile Ile Val Pro His Gln Glu His Val Leu Pro Met
                565                 570                 575 atc cca agc ggt ggt gct ttc aag gac atg atc atg gag ggt gat ggc   1776
Ile Pro Ser Gly Gly Ala Phe Lys Asp Met Ile Met Glu Gly Asp Gly
                580                 585                 590 agg acc tcg tac                                                   1788
Arg Thr Ser Tyr
        595

<210> SEQ ID NO 2
<211> LENGTH: 596
<212> TYPE: PRT
<213> ORGANISM: Triticum aestivum

<400> SEQUENCE: 2

Ser Pro Ala Ala Thr Ser Ala Ala Pro Pro Ala Thr Ala Leu Arg Pro
1               5                   10                  15

Trp Gly Pro Ser Glu Pro Arg Lys Gly Ala Asp Ile Leu Val Glu Ala
            20                  25                  30

Leu Glu Arg Cys Gly Ile Val Asp Val Phe Ala Tyr Pro Gly Gly Thr
        35                  40                  45

Ser Met Glu Ile His Gln Ala Leu Thr Arg Ser Pro Val Ile Thr Asn
    50                  55                  60

His Leu Phe Arg His Glu Gln Gly Glu Ala Phe Ala Ala Ser Gly Tyr
65                  70                  75                  80

Ala Arg Ala Ser Gly Arg Val Gly Val Cys Val Ala Thr Ser Gly Pro
                85                  90                  95

Gly Ala Thr Asn Leu Val Ser Ala Leu Ala Asp Ala Leu Leu Asp Ser
            100                 105                 110

Ile Pro Met Val Ala Ile Thr Gly Gln Val Pro Arg Arg Met Ile Gly
        115                 120                 125

Thr Asp Ala Phe Gln Glu Thr Pro Ile Val Glu Val Thr Arg Ser Ile
    130                 135                 140

Thr Lys His Asn Tyr Leu Val Leu Asp Val Glu Asp Ile Pro Arg Val
145                 150                 155                 160

Ile Gln Glu Ala Phe Phe Leu Ala Ser Ser Gly Arg Pro Gly Pro Val
                165                 170                 175

Leu Val Asp Ile Pro Lys Asp Ile Gln Gln Met Ala Val Pro Val
            180                 185                 190

Trp Asp Thr Pro Met Ser Leu Pro Gly Tyr Ile Ala Arg Leu Pro Lys
        195                 200                 205

Pro Pro Ser Thr Glu Ser Leu Glu Gln Val Leu Arg Leu Val Gly Glu
    210                 215                 220

Ser Arg Arg Pro Ile Leu Tyr Val Gly Gly Gly Cys Ala Ala Ser Gly
225                 230                 235                 240

Glu Glu Leu Arg Arg Phe Val Glu Leu Thr Gly Ile Pro Val Thr Thr
                245                 250                 255

Thr Leu Met Gly Leu Gly Asn Phe Pro Ser Asp Asp Pro Leu Ser Leu
            260                 265                 270

Arg Met Leu Gly Met His Gly Thr Val Tyr Ala Asn Tyr Ala Val Asp
        275                 280                 285
```

```
Lys Ala Asp Leu Leu Leu Ala Phe Gly Val Arg Phe Asp Asp Arg Val
    290                 295                 300
Thr Gly Lys Ile Glu Ala Phe Ala Ser Arg Ser Lys Ile Val His Ile
305                 310                 315                 320
Asp Ile Asp Pro Ala Glu Ile Gly Lys Asn Lys Gln Pro His Val Ser
                325                 330                 335
Ile Cys Ala Asp Val Lys Leu Ala Leu Gln Gly Leu Asn Asp Leu Leu
            340                 345                 350
Asn Gly Ser Lys Ala Gln Gln Gly Leu Asp Phe Gly Pro Trp His Lys
        355                 360                 365
Glu Leu Asp Gln Gln Lys Arg Glu Phe Pro Leu Gly Phe Lys Thr Phe
370                 375                 380
Gly Glu Ala Ile Pro Pro Gln Tyr Ala Ile Gln Val Leu Asp Glu Leu
385                 390                 395                 400
Thr Lys Gly Glu Ala Ile Ile Ala Thr Gly Val Gly Gln His Gln Met
                405                 410                 415
Trp Ala Ala Gln Tyr Tyr Thr Tyr Lys Arg Pro Arg Gln Trp Leu Ser
            420                 425                 430
Ser Ser Gly Leu Gly Ala Met Gly Phe Gly Leu Pro Ala Ala Ala Gly
        435                 440                 445
Ala Ala Val Ala Asn Pro Gly Val Thr Val Val Asp Ile Asp Gly Asp
450                 455                 460
Gly Ser Phe Leu Met Asn Ile Gln Glu Leu Ala Leu Ile Arg Ile Glu
465                 470                 475                 480
Asn Leu Pro Val Lys Val Met Ile Leu Asn Asn Gln His Leu Gly Met
                485                 490                 495
Val Val Gln Trp Glu Asp Arg Phe Tyr Lys Ala Asn Arg Ala His Thr
            500                 505                 510
Tyr Leu Gly Asn Pro Glu Asn Glu Ser Glu Ile Tyr Pro Asp Phe Val
        515                 520                 525
Thr Ile Ala Lys Gly Phe Asn Val Pro Ala Val Arg Val Thr Lys Lys
530                 535                 540
Ser Glu Val Thr Ala Ala Ile Lys Lys Met Leu Glu Thr Pro Gly Pro
545                 550                 555                 560
Tyr Leu Leu Asp Ile Ile Val Pro His Gln Glu His Val Leu Pro Met
                565                 570                 575
Ile Pro Ser Gly Gly Ala Phe Lys Asp Met Ile Met Glu Gly Asp Gly
            580                 585                 590
Arg Thr Ser Tyr
        595

<210> SEQ ID NO 3
<211> LENGTH: 1788
<212> TYPE: DNA
<213> ORGANISM: Triticum aestivum
<220> FEATURE:
<221> NAME/KEY: CDS
<222> LOCATION: (1)...(1788)

<400> SEQUENCE: 3 tcc ccc gcc gcc acc tcc gcc gcg cct ccc gca acc gcg ctc cgg ccc     48
Ser Pro Ala Ala Thr Ser Ala Ala Pro Pro Ala Thr Ala Leu Arg Pro
1               5                   10                  15 tgg ggc ccg tcc gag ccc cgc aag ggc gcc gac atc ctc gtc gag gcg     96
Trp Gly Pro Ser Glu Pro Arg Lys Gly Ala Asp Ile Leu Val Glu Ala
            20                  25                  30
```

```
                                                          -continued
ctc gag cgc tgc ggc atc gtc gac gtc ttc gcc tac ccc ggc ggc gcc    144
Leu Glu Arg Cys Gly Ile Val Asp Val Phe Ala Tyr Pro Gly Gly Ala
         35                  40                  45 tcc atg gag atc cac cag gcg ctg acg cgc tcg ccc gtc atc acc aac    192
Ser Met Glu Ile His Gln Ala Leu Thr Arg Ser Pro Val Ile Thr Asn
 50                  55                  60 cac ctc ttc cgc cac gag cag ggg gag gcg ttc gcg gcg tcc ggc tac    240
His Leu Phe Arg His Glu Gln Gly Glu Ala Phe Ala Ala Ser Gly Tyr
 65                  70                  75                  80 gcc cgc gcg tcc ggc cgc gtc ggc gtc tgc gtc gcc acc tcc ggc ccg    288
Ala Arg Ala Ser Gly Arg Val Gly Val Cys Val Ala Thr Ser Gly Pro
                 85                  90                  95 ggg gcc acc aac ctc gtc tcc gcg ctc gcc gac gcc ctc ctc gac tcc    336
Gly Ala Thr Asn Leu Val Ser Ala Leu Ala Asp Ala Leu Leu Asp Ser
            100                 105                 110 atc ccc atg gtc gcc atc acg ggc cag gtc ccc cgc cgc atg atc ggc    384
Ile Pro Met Val Ala Ile Thr Gly Gln Val Pro Arg Arg Met Ile Gly
        115                 120                 125 acg gac gcg ttc cag gag acg ccc ata gtg gag gtc acg cgc tcc atc    432
Thr Asp Ala Phe Gln Glu Thr Pro Ile Val Glu Val Thr Arg Ser Ile
    130                 135                 140 acc aag cac aac tac ctg gtc ctt gac gtg gag gat atc ccc cgc gtc    480
Thr Lys His Asn Tyr Leu Val Leu Asp Val Glu Asp Ile Pro Arg Val
145                 150                 155                 160 atc cag gaa gcc ttc ttc ctt gca tcc tct ggc cgc ccg ggg ccg gtg    528
Ile Gln Glu Ala Phe Phe Leu Ala Ser Ser Gly Arg Pro Gly Pro Val
                165                 170                 175 cta gtt gat atc ccc aag gac atc cag cag cag atg gct gtg ccc gtc    576
Leu Val Asp Ile Pro Lys Asp Ile Gln Gln Gln Met Ala Val Pro Val
            180                 185                 190 tgg gac act cca atg agt ttg cca ggg tac atc gcc cgc ctg ccc aag    624
Trp Asp Thr Pro Met Ser Leu Pro Gly Tyr Ile Ala Arg Leu Pro Lys
        195                 200                 205 cca cca tct act gaa tcg ctt gag cag gtc ctg cgt ctg gtt ggc gag    672
Pro Pro Ser Thr Glu Ser Leu Glu Gln Val Leu Arg Leu Val Gly Glu
    210                 215                 220 tca cgg cgc cca att ctg tat gtt ggt ggt ggc tgc gct gcg tct ggc    720
Ser Arg Arg Pro Ile Leu Tyr Val Gly Gly Gly Cys Ala Ala Ser Gly
225                 230                 235                 240 gag gag ttg cgc cgc ttt gtt gag ctt act ggg att cca gtt aca act    768
Glu Glu Leu Arg Arg Phe Val Glu Leu Thr Gly Ile Pro Val Thr Thr
                245                 250                 255 act ctg atg ggc ctt ggc aac ttc ccc agc gac gac cca ctg tct ctg    816
Thr Leu Met Gly Leu Gly Asn Phe Pro Ser Asp Asp Pro Leu Ser Leu
            260                 265                 270 cgc atg ctt ggg atg cat ggc act gtg tat gca aat tat gca gta gat    864
Arg Met Leu Gly Met His Gly Thr Val Tyr Ala Asn Tyr Ala Val Asp
        275                 280                 285 aag gct gac ctg ttg ctc gca ttt ggt gtg cgg ttt gat gat cgt gtg    912
Lys Ala Asp Leu Leu Leu Ala Phe Gly Val Arg Phe Asp Asp Arg Val
    290                 295                 300 act ggg aaa atc gag gct ttt gca agc agg tcc aag att gtg cac att    960
Thr Gly Lys Ile Glu Ala Phe Ala Ser Arg Ser Lys Ile Val His Ile
305                 310                 315                 320 gac att gac cca gct gag att ggc aag aac aag cag cca cat gtc tcc   1008
Asp Ile Asp Pro Ala Glu Ile Gly Lys Asn Lys Gln Pro His Val Ser
                325                 330                 335 att tgt gca gat gtt aag ctt gct tta cag ggg ttg aat gat cta tta   1056
Ile Cys Ala Asp Val Lys Leu Ala Leu Gln Gly Leu Asn Asp Leu Leu
            340                 345                 350
```

```
aat ggg agc aaa gca caa cag ggt ctg gat ttt ggt cca tgg cac aag    1104
Asn Gly Ser Lys Ala Gln Gln Gly Leu Asp Phe Gly Pro Trp His Lys
        355                 360                 365 gag ttg gat cag cag aag agg gag ttt cct cta gga ttc aag act ttt    1152
Glu Leu Asp Gln Gln Lys Arg Glu Phe Pro Leu Gly Phe Lys Thr Phe
    370                 375                 380 ggc gag gcc atc ccg ccg caa tat gct atc cag gta ctg gat gag ctg    1200
Gly Glu Ala Ile Pro Pro Gln Tyr Ala Ile Gln Val Leu Asp Glu Leu
385                 390                 395                 400 aca aaa ggg gag gcg atc att gcc act ggt gtt ggg cag cac cag atg    1248
Thr Lys Gly Glu Ala Ile Ile Ala Thr Gly Val Gly Gln His Gln Met
            405                 410                 415 tgg gcg gct cag tat tac act tac aag cgg cca cgg cag tgg ctg tct    1296
Trp Ala Ala Gln Tyr Tyr Thr Tyr Lys Arg Pro Arg Gln Trp Leu Ser
        420                 425                 430 tcg tct ggt ttg ggg gca atg gga ttt ggg tta cca gct gca gct ggc    1344
Ser Ser Gly Leu Gly Ala Met Gly Phe Gly Leu Pro Ala Ala Ala Gly
            435                 440                 445 gct gct gtg gcc aac cca ggt gtt aca gtt gtt gac att gat ggt gat    1392
Ala Ala Val Ala Asn Pro Gly Val Thr Val Val Asp Ile Asp Gly Asp
450                 455                 460 ggt agt ttc ctc atg aac att cag gag ttg gcg ttg atc cgc att gag    1440
Gly Ser Phe Leu Met Asn Ile Gln Glu Leu Ala Leu Ile Arg Ile Glu
465                 470                 475                 480 aac ctc cca gtg aag gtg atg ata ttg aac aac cag cat ctg gga atg    1488
Asn Leu Pro Val Lys Val Met Ile Leu Asn Asn Gln His Leu Gly Met
            485                 490                 495 gtg gtg cag tgg gag gat agg ttt tac aag gcc aat cgg gcg cac aca    1536
Val Val Gln Trp Glu Asp Arg Phe Tyr Lys Ala Asn Arg Ala His Thr
        500                 505                 510 tac ctt ggc aac cca gaa aat gag agt gag ata tat cca gat ttt gtg    1584
Tyr Leu Gly Asn Pro Glu Asn Glu Ser Glu Ile Tyr Pro Asp Phe Val
            515                 520                 525 acg att gct aaa gga ttc aac gtt cca gca gtt cga gtg acg aag aag    1632
Thr Ile Ala Lys Gly Phe Asn Val Pro Ala Val Arg Val Thr Lys Lys
        530                 535                 540 agc gaa gtc act gca gca atc aag aag atg ctt gag acc cca ggg cca    1680
Ser Glu Val Thr Ala Ala Ile Lys Lys Met Leu Glu Thr Pro Gly Pro
545                 550                 555                 560 tac ttg ttg gat atc ata gtc ccg cat cag gag cac gtg ctg cct atg    1728
Tyr Leu Leu Asp Ile Ile Val Pro His Gln Glu His Val Leu Pro Met
            565                 570                 575 atc cca agc ggt ggt gct ttc aag gac atg atc atg gag ggt gat ggc    1776
Ile Pro Ser Gly Gly Ala Phe Lys Asp Met Ile Met Glu Gly Asp Gly
        580                 585                 590 agg acc tcg tac                                                    1788
Arg Thr Ser Tyr
        595

<210> SEQ ID NO 4
<211> LENGTH: 596
<212> TYPE: PRT
<213> ORGANISM: Triticum aestivum

<400> SEQUENCE: 4

Ser Pro Ala Ala Thr Ser Ala Ala Pro Pro Ala Thr Ala Leu Arg Pro
1               5                   10                  15

Trp Gly Pro Ser Glu Pro Arg Lys Gly Ala Asp Ile Leu Val Glu Ala
            20                  25                  30
```

Leu Glu Arg Cys Gly Ile Val Asp Val Phe Ala Tyr Pro Gly Gly Ala
             35                  40                  45

Ser Met Glu Ile His Gln Ala Leu Thr Arg Ser Pro Val Ile Thr Asn
 50                  55                  60

His Leu Phe Arg His Glu Gln Gly Glu Ala Phe Ala Ala Ser Gly Tyr
 65                  70                  75                  80

Ala Arg Ala Ser Gly Arg Val Gly Val Cys Val Ala Thr Ser Gly Pro
                 85                  90                  95

Gly Ala Thr Asn Leu Val Ser Ala Leu Ala Asp Ala Leu Leu Asp Ser
             100                 105                 110

Ile Pro Met Val Ala Ile Thr Gly Gln Val Pro Arg Arg Met Ile Gly
             115                 120                 125

Thr Asp Ala Phe Gln Glu Thr Pro Ile Val Glu Val Thr Arg Ser Ile
 130                 135                 140

Thr Lys His Asn Tyr Leu Val Leu Asp Val Glu Asp Ile Pro Arg Val
 145                 150                 155                 160

Ile Gln Glu Ala Phe Phe Leu Ala Ser Ser Gly Arg Pro Gly Pro Val
                 165                 170                 175

Leu Val Asp Ile Pro Lys Asp Ile Gln Gln Gln Met Ala Val Pro Val
             180                 185                 190

Trp Asp Thr Pro Met Ser Leu Pro Gly Tyr Ile Ala Arg Leu Pro Lys
             195                 200                 205

Pro Pro Ser Thr Glu Ser Leu Glu Gln Val Leu Arg Leu Val Gly Glu
 210                 215                 220

Ser Arg Arg Pro Ile Leu Tyr Val Gly Gly Gly Cys Ala Ala Ser Gly
 225                 230                 235                 240

Glu Glu Leu Arg Arg Phe Val Glu Leu Thr Gly Ile Pro Val Thr Thr
                 245                 250                 255

Thr Leu Met Gly Leu Gly Asn Phe Pro Ser Asp Asp Pro Leu Ser Leu
             260                 265                 270

Arg Met Leu Gly Met His Gly Thr Val Tyr Ala Asn Tyr Ala Val Asp
             275                 280                 285

Lys Ala Asp Leu Leu Leu Ala Phe Gly Val Arg Phe Asp Asp Arg Val
 290                 295                 300

Thr Gly Lys Ile Glu Ala Phe Ala Ser Arg Ser Lys Ile Val His Ile
 305                 310                 315                 320

Asp Ile Asp Pro Ala Glu Ile Gly Lys Asn Lys Gln Pro His Val Ser
                 325                 330                 335

Ile Cys Ala Asp Val Lys Leu Ala Leu Gln Gly Leu Asn Asp Leu Leu
             340                 345                 350

Asn Gly Ser Lys Ala Gln Gln Gly Leu Asp Phe Gly Pro Trp His Lys
             355                 360                 365

Glu Leu Asp Gln Gln Lys Arg Glu Phe Pro Leu Gly Phe Lys Thr Phe
 370                 375                 380

Gly Glu Ala Ile Pro Pro Gln Tyr Ala Ile Gln Val Leu Asp Glu Leu
 385                 390                 395                 400

Thr Lys Gly Glu Ala Ile Ile Ala Thr Gly Val Gly Gln His Gln Met
                 405                 410                 415

Trp Ala Ala Gln Tyr Tyr Thr Tyr Lys Arg Pro Arg Gln Trp Leu Ser
             420                 425                 430

Ser Ser Gly Leu Gly Ala Met Gly Phe Gly Leu Pro Ala Ala Ala Gly
             435                 440                 445

Ala Ala Val Ala Asn Pro Gly Val Thr Val Val Asp Ile Asp Gly Asp

```
                    450                 455                 460
Gly Ser Phe Leu Met Asn Ile Gln Glu Leu Ala Leu Ile Arg Ile Glu
465                 470                 475                 480

Asn Leu Pro Val Lys Val Met Ile Leu Asn Asn Gln His Leu Gly Met
                    485                 490                 495

Val Val Gln Trp Glu Asp Arg Phe Tyr Lys Ala Asn Arg Ala His Thr
                500                 505                 510

Tyr Leu Gly Asn Pro Glu Asn Glu Ser Glu Ile Tyr Pro Asp Phe Val
                515                 520                 525

Thr Ile Ala Lys Gly Phe Asn Val Pro Ala Val Arg Val Thr Lys Lys
                530                 535                 540

Ser Glu Val Thr Ala Ala Ile Lys Lys Met Leu Glu Thr Pro Gly Pro
545                 550                 555                 560

Tyr Leu Leu Asp Ile Ile Val Pro His Gln Glu His Val Leu Pro Met
                565                 570                 575

Ile Pro Ser Gly Gly Ala Phe Lys Asp Met Ile Met Glu Gly Asp Gly
                580                 585                 590

Arg Thr Ser Tyr
        595

<210> SEQ ID NO 5
<211> LENGTH: 1788
<212> TYPE: DNA
<213> ORGANISM: Triticum aestivum
<220> FEATURE:
<221> NAME/KEY: CDS
<222> LOCATION: (1)...(1788)
<221> NAME/KEY: misc_feature
<222> LOCATION: 142
<223> OTHER INFORMATION: R = G or A

<400> SEQUENCE: 5 tcc ccc gcc gcc acc tcc gcc gcg cct ccc gca acc gcg ctc cgg ccc      48
Ser Pro Ala Ala Thr Ser Ala Ala Pro Pro Ala Thr Ala Leu Arg Pro
1               5                   10                  15 tgg ggc ccg tcc gag ccc cgc aag ggc gcc gac atc ctc gtc gag gcg      96
Trp Gly Pro Ser Glu Pro Arg Lys Gly Ala Asp Ile Leu Val Glu Ala
            20                  25                  30 ctc gag cgc tgc ggc atc gtc gac gtc ttc gcc tac ccc ggc ggc rcc     144
Leu Glu Arg Cys Gly Ile Val Asp Val Phe Ala Tyr Pro Gly Gly Xaa
        35                  40                  45 tcc atg gag atc cac cag gcg ctg acg cgc tcg ccc gtc atc acc aac     192
Ser Met Glu Ile His Gln Ala Leu Thr Arg Ser Pro Val Ile Thr Asn
50                  55                  60 cac ctc ttc cgc cac gag cag ggg gag gcg ttc gcg gcg tcc ggc tac     240
His Leu Phe Arg His Glu Gln Gly Glu Ala Phe Ala Ala Ser Gly Tyr
65                  70                  75                  80 gcc cgc gcg tcc ggc cgc gtc ggc gtc tgc gtc gcc acc tcc ggc ccg     288
Ala Arg Ala Ser Gly Arg Val Gly Val Cys Val Ala Thr Ser Gly Pro
                85                  90                  95 ggg gcc acc aac ctc gtc tcc gcg ctc gcc gac gcc ctc ctc gac tcc     336
Gly Ala Thr Asn Leu Val Ser Ala Leu Ala Asp Ala Leu Leu Asp Ser
            100                 105                 110 atc ccc atg gtc gcc atc acg ggc cag gtc ccc cgc cgc atg atc ggc     384
Ile Pro Met Val Ala Ile Thr Gly Gln Val Pro Arg Arg Met Ile Gly
        115                 120                 125 acg gac gcg ttc cag gag acg ccc ata gtg gag gtc acg cgc tcc atc     432
Thr Asp Ala Phe Gln Glu Thr Pro Ile Val Glu Val Thr Arg Ser Ile
130                 135                 140
```

```
acc aag cac aac tac ctg gtc ctt gac gtg gag gat atc ccc cgc gtc      480
Thr Lys His Asn Tyr Leu Val Leu Asp Val Glu Asp Ile Pro Arg Val
145                 150                 155                 160 atc cag gaa gcc ttc ttc ctt gca tcc tct ggc cgc ccg ggg ccg gtg      528
Ile Gln Glu Ala Phe Phe Leu Ala Ser Ser Gly Arg Pro Gly Pro Val
                165                 170                 175 cta gtt gat atc ccc aag gac atc cag cag cag atg gct gtg ccc gtc      576
Leu Val Asp Ile Pro Lys Asp Ile Gln Gln Gln Met Ala Val Pro Val
            180                 185                 190 tgg gac act cca atg agt ttg cca ggg tac atc gcc cgc ctg ccc aag      624
Trp Asp Thr Pro Met Ser Leu Pro Gly Tyr Ile Ala Arg Leu Pro Lys
        195                 200                 205 cca cca tct act gaa tcg ctt gag cag gtc ctg cgt ctg gtt ggc gag      672
Pro Pro Ser Thr Glu Ser Leu Glu Gln Val Leu Arg Leu Val Gly Glu
    210                 215                 220 tca cgg cgc cca att ctg tat gtt ggt ggt ggc tgc gct gcg tct ggc      720
Ser Arg Arg Pro Ile Leu Tyr Val Gly Gly Gly Cys Ala Ala Ser Gly
225                 230                 235                 240 gag gag ttg cgc cgc ttt gtt gag ctt act ggg att cca gtt aca act      768
Glu Glu Leu Arg Arg Phe Val Glu Leu Thr Gly Ile Pro Val Thr Thr
                245                 250                 255 act ctg atg ggc ctt ggc aac ttc ccc agc gac gac cca ctg tct ctg      816
Thr Leu Met Gly Leu Gly Asn Phe Pro Ser Asp Asp Pro Leu Ser Leu
            260                 265                 270 cgc atg ctt ggg atg cat ggc act gtg tat gca aat tat gca gta gat      864
Arg Met Leu Gly Met His Gly Thr Val Tyr Ala Asn Tyr Ala Val Asp
        275                 280                 285 aag gct gac ctg ttg ctc gca ttt ggt gtg cgg ttt gat gat cgt gtg      912
Lys Ala Asp Leu Leu Leu Ala Phe Gly Val Arg Phe Asp Asp Arg Val
    290                 295                 300 act ggg aaa atc gag gct ttt gca agc agg tcc aag att gtg cac att      960
Thr Gly Lys Ile Glu Ala Phe Ala Ser Arg Ser Lys Ile Val His Ile
305                 310                 315                 320 gac att gac cca gct gag att ggc aag aac aag cag cca cat gtc tcc     1008
Asp Ile Asp Pro Ala Glu Ile Gly Lys Asn Lys Gln Pro His Val Ser
                325                 330                 335 att tgt gca gat gtt aag ctt gct tta cag ggg ttg aat gat cta tta     1056
Ile Cys Ala Asp Val Lys Leu Ala Leu Gln Gly Leu Asn Asp Leu Leu
            340                 345                 350 aat ggg agc aaa gca caa cag ggt ctg gat ttt ggt cca tgg cac aag     1104
Asn Gly Ser Lys Ala Gln Gln Gly Leu Asp Phe Gly Pro Trp His Lys
        355                 360                 365 gag ttg gat cag cag aag agg gag ttt cct cta gga ttc aag act ttt     1152
Glu Leu Asp Gln Gln Lys Arg Glu Phe Pro Leu Gly Phe Lys Thr Phe
    370                 375                 380 ggc gag gcc atc ccg ccg caa tat gct atc cag gta ctg gat gag ctg     1200
Gly Glu Ala Ile Pro Pro Gln Tyr Ala Ile Gln Val Leu Asp Glu Leu
385                 390                 395                 400 aca aaa ggg gag gcg atc att gcc act ggt gtt ggg cag cac cag atg     1248
Thr Lys Gly Glu Ala Ile Ile Ala Thr Gly Val Gly Gln His Gln Met
                405                 410                 415 tgg gcg gct cag tat tac act tac aag cgg cca cgg cag tgg ctg tct     1296
Trp Ala Ala Gln Tyr Tyr Thr Tyr Lys Arg Pro Arg Gln Trp Leu Ser
            420                 425                 430 tcg tct ggt ttg ggg gca atg gga ttt ggg tta cca gct gca gct ggc     1344
Ser Ser Gly Leu Gly Ala Met Gly Phe Gly Leu Pro Ala Ala Ala Gly
        435                 440                 445 gct gct gtg gcc aac cca ggt gtt aca gtt gtt gac att gat ggt gat     1392
Ala Ala Val Ala Asn Pro Gly Val Thr Val Val Asp Ile Asp Gly Asp
    450                 455                 460
```

```
ggt agt ttc ctc atg aac att cag gag ttg gcg ttg atc cgc att gag      1440
Gly Ser Phe Leu Met Asn Ile Gln Glu Leu Ala Leu Ile Arg Ile Glu
465                 470                 475                 480 aac ctc cca gtg aag gtg atg ata ttg aac aac cag cat ctg gga atg      1488
Asn Leu Pro Val Lys Val Met Ile Leu Asn Asn Gln His Leu Gly Met
                485                 490                 495 gtg gtg cag tgg gag gat agg ttt tac aag gcc aat cgg gcg cac aca      1536
Val Val Gln Trp Glu Asp Arg Phe Tyr Lys Ala Asn Arg Ala His Thr
            500                 505                 510 tac ctt ggc aac cca gaa aat gag agt gag ata tat cca gat ttt gtg      1584
Tyr Leu Gly Asn Pro Glu Asn Glu Ser Glu Ile Tyr Pro Asp Phe Val
        515                 520                 525 acg att gct aaa gga ttc aac gtt cca gca gtt cga gtg acg aag aag      1632
Thr Ile Ala Lys Gly Phe Asn Val Pro Ala Val Arg Val Thr Lys Lys
    530                 535                 540 agc gaa gtc act gca gca atc aag aag atg ctt gag acc cca ggg cca      1680
Ser Glu Val Thr Ala Ala Ile Lys Lys Met Leu Glu Thr Pro Gly Pro
545                 550                 555                 560 tac ttg ttg gat atc ata gtc ccg cat cag gag cac gtg ctg cct atg      1728
Tyr Leu Leu Asp Ile Ile Val Pro His Gln Glu His Val Leu Pro Met
                565                 570                 575 atc cca agc ggt ggt gct ttc aag gac atg atc atg gag ggt gat ggc      1776
Ile Pro Ser Gly Gly Ala Phe Lys Asp Met Ile Met Glu Gly Asp Gly
            580                 585                 590 agg acc tcg tac                                                      1788
Arg Thr Ser Tyr
        595

<210> SEQ ID NO 6
<211> LENGTH: 596
<212> TYPE: PRT
<213> ORGANISM: Triticum aestivum
<220> FEATURE:
<221> NAME/KEY: UNSURE
<222> LOCATION: (48)...(48)
<223> OTHER INFORMATION: Xaa = Thr or Ala

<400> SEQUENCE: 6

Ser Pro Ala Ala Thr Ser Ala Ala Pro Pro Ala Thr Ala Leu Arg Pro
1               5                   10                  15

Trp Gly Pro Ser Glu Pro Arg Lys Gly Ala Asp Ile Leu Val Glu Ala
            20                  25                  30

Leu Glu Arg Cys Gly Ile Val Asp Val Phe Ala Tyr Pro Gly Gly Xaa
        35                  40                  45

Ser Met Glu Ile His Gln Ala Leu Thr Arg Ser Pro Val Ile Thr Asn
    50                  55                  60

His Leu Phe Arg His Glu Gln Gly Glu Ala Phe Ala Ala Ser Gly Tyr
65                  70                  75                  80

Ala Arg Ala Ser Gly Arg Val Gly Val Cys Val Ala Thr Ser Gly Pro
                85                  90                  95

Gly Ala Thr Asn Leu Val Ser Ala Leu Ala Asp Ala Leu Leu Asp Ser
            100                 105                 110

Ile Pro Met Val Ala Ile Thr Gly Gln Val Pro Arg Arg Met Ile Gly
        115                 120                 125

Thr Asp Ala Phe Gln Glu Thr Pro Ile Val Glu Val Thr Arg Ser Ile
    130                 135                 140

Thr Lys His Asn Tyr Leu Val Leu Asp Val Glu Asp Ile Pro Arg Val
145                 150                 155                 160
```

```
Ile Gln Glu Ala Phe Phe Leu Ala Ser Ser Gly Arg Pro Gly Pro Val
                165                 170                 175

Leu Val Asp Ile Pro Lys Asp Ile Gln Gln Met Ala Val Pro Val
            180                 185                 190

Trp Asp Thr Pro Met Ser Leu Pro Gly Tyr Ile Ala Arg Leu Pro Lys
            195                 200                 205

Pro Pro Ser Thr Glu Ser Leu Glu Gln Val Leu Arg Leu Val Gly Glu
            210                 215                 220

Ser Arg Arg Pro Ile Leu Tyr Val Gly Gly Cys Ala Ala Ser Gly
225                 230                 235                 240

Glu Glu Leu Arg Arg Phe Val Glu Leu Thr Gly Ile Pro Val Thr Thr
                245                 250                 255

Thr Leu Met Gly Leu Gly Asn Phe Pro Ser Asp Asp Pro Leu Ser Leu
            260                 265                 270

Arg Met Leu Gly Met His Gly Thr Val Tyr Ala Asn Tyr Ala Val Asp
            275                 280                 285

Lys Ala Asp Leu Leu Leu Ala Phe Gly Val Arg Phe Asp Asp Arg Val
            290                 295                 300

Thr Gly Lys Ile Glu Ala Phe Ala Ser Arg Ser Lys Ile Val His Ile
305                 310                 315                 320

Asp Ile Asp Pro Ala Glu Ile Gly Lys Asn Lys Gln Pro His Val Ser
                325                 330                 335

Ile Cys Ala Asp Val Lys Leu Ala Leu Gln Gly Leu Asn Asp Leu Leu
            340                 345                 350

Asn Gly Ser Lys Ala Gln Gln Gly Leu Asp Phe Gly Pro Trp His Lys
            355                 360                 365

Glu Leu Asp Gln Gln Lys Arg Glu Phe Pro Leu Gly Phe Lys Thr Phe
            370                 375                 380

Gly Glu Ala Ile Pro Pro Gln Tyr Ala Ile Gln Val Leu Asp Glu Leu
385                 390                 395                 400

Thr Lys Gly Glu Ala Ile Ile Ala Thr Gly Val Gly Gln His Gln Met
                405                 410                 415

Trp Ala Ala Gln Tyr Tyr Thr Tyr Lys Arg Pro Arg Gln Trp Leu Ser
            420                 425                 430

Ser Ser Gly Leu Gly Ala Met Gly Phe Gly Leu Pro Ala Ala Ala Gly
            435                 440                 445

Ala Ala Val Ala Asn Pro Gly Val Thr Val Val Asp Ile Asp Gly Asp
            450                 455                 460

Gly Ser Phe Leu Met Asn Ile Gln Glu Leu Ala Leu Ile Arg Ile Glu
465                 470                 475                 480

Asn Leu Pro Val Lys Val Met Ile Leu Asn Asn Gln His Leu Gly Met
                485                 490                 495

Val Val Gln Trp Glu Asp Arg Phe Tyr Lys Ala Asn Arg Ala His Thr
            500                 505                 510

Tyr Leu Gly Asn Pro Glu Asn Glu Ser Glu Ile Tyr Pro Asp Phe Val
            515                 520                 525

Thr Ile Ala Lys Gly Phe Asn Val Pro Ala Val Arg Val Thr Lys Lys
            530                 535                 540

Ser Glu Val Thr Ala Ala Ile Lys Lys Met Leu Glu Thr Pro Gly Pro
545                 550                 555                 560

Tyr Leu Leu Asp Ile Ile Val Pro His Gln Glu His Val Leu Pro Met
                565                 570                 575
```

```
Ile Pro Ser Gly Gly Ala Phe Lys Asp Met Ile Met Glu Gly Asp Gly
            580                 585                 590

Arg Thr Ser Tyr
        595
```